United States Patent
Keitz et al.

(10) Patent No.: US 6,998,414 B2
(45) Date of Patent: Feb. 14, 2006

(54) SUBSTITUTED ARYLAMIDES AS IP ANTAGONISTS

(75) Inventors: Paul Francis Keitz, Redwood City, CA (US); Alam Jahangir, San Jose, CA (US); Francisco Javier Lopez-Tapia, Union City, CA (US); Counde O'Yang, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 57 days.

(21) Appl. No.: 10/835,016

(22) Filed: Apr. 29, 2004

(65) Prior Publication Data

US 2004/0220247 A1 Nov. 4, 2004

Related U.S. Application Data

(60) Provisional application No. 60/467,279, filed on May 1, 2003.

(51) Int. Cl.
*A61K 31/4168* (2006.01)
*C07D 231/06* (2006.01)

(52) U.S. Cl. ................. 514/400; 548/300.1; 548/347.1; 548/348.1

(58) Field of Classification Search .............. 548/300.1, 548/347.1, 348.1; 514/400
See application file for complete search history.

(56) References Cited

U.S. PATENT DOCUMENTS

| | | | |
|---|---|---|---|
| 4,396,617 A | 8/1983 | Dolman et al. | |
| 5,741,796 A | 4/1998 | Hartman et al. | |
| 6,184,242 B1 | 2/2001 | Bley et al. | |
| 6,417,186 B1 | 7/2002 | Jahangir | |

FOREIGN PATENT DOCUMENTS

| | | |
|---|---|---|
| EP | 0017484 A1 | 10/1980 |
| EP | 0 902 018 | 3/1998 |
| WO | WO 00/72840 A1 | 12/2000 |
| WO | WO 02/40453 A1 | 5/2002 |

OTHER PUBLICATIONS

LeClerc, Gerard et al., Agents alpha–adrenergiques alcoylants, European Journal of Medicine, 1983–18, No. 4, pp. 379–383.*

* cited by examiner

*Primary Examiner*—Kamal A. Saeed
*Assistant Examiner*—Susannah E. Lee
(74) *Attorney, Agent, or Firm*—Robert C. Hall

(57) ABSTRACT

Compounds effective as IP receptor modulators, particularly IP receptor antagonists, that are of the formula I:

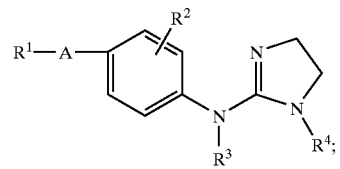

wherein A, $R^1$, $R^2$, $R^3$ and $R^4$ are as defined in the specification; and individual isomers, racemic or non-racemic mixtures of isomers, and pharmaceutically acceptable salts or solvates thereof. Also disclosed are pharmaceutical compositions containing such compounds and methods for their use as therapeutic agents.

64 Claims, No Drawings

SUBSTITUTED ARYLAMIDES AS IP ANTAGONISTS

CROSS REFERENCE

This Application claims the benefit under title 35 U.S.C. 119(e) of U.S. Provisional Application No. 60/467,279, filed May 1, 2003.

FIELD OF THE INVENTION

This invention relates to prostaglandin $I_2$ (IP) receptor antagonists, and associated pharmaceutical compositions containing them, and methods for their use as therapeutic agents.

BACKGROUND OF THE INVENTION

Prostaglandins or prostanoids (PG's) are a group of bioactive compounds derived from membrane phospholipids and are formed from 20-carbon essential fatty acids containing three, four, or five double bonds, and a cyclopentane ring. They fall into several main classes designated by the letters D, E, F, G, H, or I, and are distinguished by substitutions to the cyclopentane ring. The main classes are further subdivided by subscripts 1, 2, or 3, which reflect their fatty acid precursors. Thus, $PGI_2$ has a double ring structure, and the subscript 2 indicates that it is related to arachidonic acid.

$PGI_2$ (also known as prostacyclin) acts on platelets and blood vessels to inhibit aggregation and to cause vasodilation, and is thought to be important for vascular homeostasis. It has been suggested that $PGI_2$ may contribute to the antithrombogenic properties of the intact vascular wall. $PGI_2$ is also thought to be a physiological modulator of vascular tone that functions to oppose the actions of vasoconstrictors. The importance of these vascular actions is emphasized by the participation of $PGI_2$ in the hypotension associated with septic shock. Although prostaglandins do not appear to have direct effects on vascular permeability, $PGI_2$ markedly enhances edema formation and leukocyte infiltration by promoting blood flow in the inflamed region. Therefore, IP receptor antagonists may relieve hypotension related to septic shock, may reduce edema formation, and may prevent conditions associated with excessive bleeding such as, but not limited to, hemophilia and hemorrhaging.

Several in vivo analgesia studies in rodents suggest that $PGI_2$ plays a major role in the induction of hyperalgesia. Likewise, in vitro studies provide substantial evidence to suggest that "$PGI_2$-preferring" (IP) receptors act as important modulators of sensory neuron function (K. Bley et al, Trends in Pharmacological Sciences 1998, 19(4):141–147). Since IP receptors in sensory neurons are coupled to activation of both adenylyl cyclase and phospholipase C, and hence, cAMP-dependent protein kinase and protein kinase C, these receptors can exert powerful effects on ion channel activity and thus neurotransmitter release. Evidence of a prominent role for IP receptors in inflammatory pain has been obtained from recent studies in transgenic mice lacking the IP receptor (T. Murata et al., Nature 1997, 388, 678–682).

In addition to being mediators of hyperalgesia, prostaglandins are known to be generated locally in the bladder in response to physiologic stimuli such as stretch of the detrusor smooth muscle, injuries of the vesical mucosa, and nerve stimulation (K. Anderson, Pharmacological Reviews 1993, 45(3), 253–308). $PGI_2$ is the major prostaglandin released from the human bladder. There are suggestions that prostaglandins may be the link between detrusor muscle stretch produced by bladder filling and activation of C-fiber afferents by bladder distension. It has been proposed that prostaglandins may be involved in the pathophysiology of bladder disorders. Therefore, antagonists of prostaglandin IP receptors are expected to be useful in the treatment of such conditions.

Antagonists of IP receptors are also expected to find a utility in respiratory allergies wherein $PGI_2$ production in response to an allergen is present or in respiratory conditions such as asthma.

IP receptor antagonists, as well as a variety of other drugs, have come under increasing scrutiny with regard to cardiovascular side effects. Promising IP receptor antagonists have failed during clinical evaluation because of ventricular arrhythmias, particularly "torsade de points" (TdP), that can occur in clinical trial subjects. The mechanism by which these drugs lead to ventricular arrhythmias has been identified with modulation of the "human ether-a-go-go" or hERG ion channel. The hERG channel is a voltage-activated, inwardly-rectifying potassium channel, and is an important contributor to the repolarization of ventricular action potentials. Blockage of the hERG channel increases the duration of cardiac action potentials, which leads to prolonged ventricular depolarization. Because of the potentially fatal nature of such hERG channel modulation, IP receptor antagonists that will ultimately be useful as drugs should cause minimal or no inhibition of the hERG channel.

Additional information relating to prostaglandins and their receptors is described in Goodman & Gillman's, The Pharmacological Basis of Therapeutics, ninth edition, McGraw-Hill, New York, 1996, Chapter 26, pages 601–616.

All publications, patents, and patent applications cited herein, whether supra or infra, are each hereby incorporated by reference their entirety.

SUMMARY OF THE INVENTION

The invention provides compounds useful as IP receptor antagonists. The subject compounds are of the formula I:

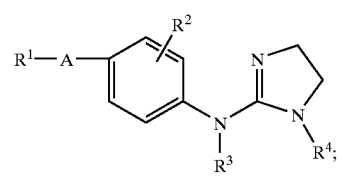

wherein:
  $R^1$ is optionally substituted aryl or optionally substituted heteroaryl;
  $R^2$ is hydrogen, alkyl, alkoxy, haloalkyl or halogen;
  $R^3$ and $R^4$ each independently is hydrogen or alkoxycarbonyl;
  A is —C(O)—NR$^a$—(CR$^b$R$^c$)$_n$— or —NR$^a$—C(O)—(CR$^b$R$^c$)$_n$—;
  n is from 1 to 6;
  $R^a$ is hydrogen, alkyl or cycloalkyl; and
  $R^b$ and $R^c$ each independently is hydrogen or alkyl;
or a pharmaceutically acceptable salt, solvate or prodrug thereof.

The invention further relates to pharmaceutical compositions comprising a therapeutically effective amount of at least one compound of formula I, or individual isomers, racemic or non-racemic mixtures of isomers, or pharmaceutically acceptable salts or solvates thereof, in admixture with at least one suitable carrier. In a preferred embodiment, the pharmaceutical compositions are suitable for administration to a subject having a disease state that is alleviated by treatment with an IP receptor antagonist.

The invention further relates to methods of preparing compounds of formula I. One such method comprises reacting a compound of the formula:

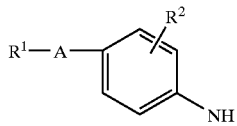

wherein R$^1$, R$^2$ and A are as defined herein,
with chloroimidazoline,
to form a compound of formula I.

The invention further relates to methods of treatment comprising administering to a subject in need of such treatment a therapeutically effective amount of at least one compound of formula I, or individual isomers, racemic or non-racemic mixtures of isomers, or pharmaceutically acceptable salts or solvates thereof.

In a preferred embodiment, the subject in need of such treatment has a disease state associated with IP receptor-mediated pain, such as inflammatory pain, neuropathic pain, cancer pain, acute pain, chronic pain, surgical pain, dental pain, premenstrual pain, visceral pain, pain due to burns, migraine or cluster headaches, neuralgias, post traumatic injuries, pain associated with functional bowel disorders such as irritable bowel syndrome, hyperalgesia, or complex regional syndromes.

In another preferred embodiment, the subject in need of such treatment has a disease state associated with IP receptor-mediated inflammation, such as bacterial, fungal infections, viral infections, idiopathic bladder inflammation, over-use, old age, nutritional deficiencies, prostatis, or conjunctivitis pain.

In another preferred embodiment, the subject in need of such treatment has a disease state associated with IP receptor-mediated urinary tract disease state, such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urge incontinence, urethritis, prostatitis, pelvic pain syndrome, prostatodynia, cystitis, or idiophatic bladder hypersensitivity.

In another preferred embodiment, the subject in need of such treatment has a disease state associated with IP receptor-mediated respiratory disease such as allergies or asthma.

In another preferred embodiment, the subject in need of such treatment has a disease state associated with IP receptor-mediated edema formation or hypotensive vascular diseases.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Acyl" (or alkanoyl) means the radical —C(O)—R, wherein R is lower alkyl as defined herein. Examples of acyl radicals include, but are not limited to, formyl, acetyl, propionyl, butyryl, and the like.

"Alkyl" means the monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means the radical —O—R, wherein R is a lower alkyl radical as defined herein. Examples of alkoxy radicals include, but are not limited to, methoxy, ethoxy, isopropoxy, and the like.

"Alkoxyalkyl" means a moiety of the formula R$^a$—O—R$^b$—, where R$^a$ is alkyl and R$^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylamino" means the radical —NHR$^d$, wherein R$^d$ is a lower alkyl radical as defined herein. Examples of alkylamino radicals include, but are not limited to, methylamino, ethylamino, butylamino, and the like.

"Alkylsulfonyl" means the radical —SO$_2$R$^f$ wherein R$^f$ is a lower alkyl radical as defined herein. Examples of alkylsulfonyl radicals include, but are not limited to, methanesulfonyl, ethanesulfonyl, propanesulfonyl, and the like.

"Alkylsulfonylalkyl" means a moiety of the formula —R'—R"—R'" where R' is alkyl, R" is —SO$_2$— and R'" is alkyl as defined herein.

"Alkylsulfamoyl" means a moiety of the formula —SO$_2$—NHR' wherein R' is alkyl as defined herein.

"Dialkylsulfamoyl" means a moiety of the formula —SO$_2$—NHR'R" wherein R' and R" are alkyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means the radical —O—R', wherein R' is an aryl radical as defined herein. Examples of aryloxy radicals include, but are not limited to, phenoxy and the like.

"Aralkyl" means the radical —R'R" wherein R' is an alkylene radical as defined herein, and R" is a lower aryl radical as defined herein. Examples of aralkyl radicals include, but are not limited to, benzyl, phenylethyl, 3-phenylpropyl, and the like.

"Aralkyloxy" means the radical —O—R', wherein R' is an aralkyl radical as defined herein. Examples of aralkyloxy radicals include, but are not limited to, benzyloxy, phenylethyloxy, and the like.

"Cycloalkyl" means the monovalent saturated carbocyclic radical consisting of one or more rings, which can be optionally substituted with one or more substituents independently selected from hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of cycloalkyl radicals include, but are not limited to, cyclopropyl, cyclobutyl, 3-ethylcyclobutyl, cyclopentyl, cyclopentyl, cycloheptyl, and the like.

"Cycloalkyloxy" means the radical —OR' wherein R' is cycloalkyl as defined herein.

"Cycloalkylalkyl" means a radical of the formula —R'R" wherein R' is alkylene as defined herein and R" is cycloalkyl as defined herein.

"Cycloalkylalkoxy" means a radical of the formula —OR'R" wherein R' is alkylene as defined herein and R" is cycloalkyl as defined herein.

"Dialkylamino" means the radical —NR'R" wherein R' and R" are each independently lower alkyl radicals as defined herein. Examples of dialkylamino radicals include, but are not limited to, dimethylamino, methyl ethylamino, diethylamino, methyl propylamino, and the like.

"Ethylenedioxy" means the radical —OCH$_2$CH$_2$O—.

"Halogen" or "halo" means the radical fluoro, bromo, chloro, and/or iodo.

"Haloalkyl" means alkyl as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiozolyl, benzothiadiazolyl, benzopyranyl, indolyl, isoindolyl, azaindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocycyloxy" means a radical —O—R wherein R is heterocyclyl as defined herein.

"Heterocycylalkyloxy" means a radical —O—R'—R" wherein R' is alkylene as defined herein and R" is heterocyclyl as defined herein.

"Heterocycylsulfonyl" means a radical —SO$_2$—R' wherein R' is alkyl as defined herein.

"Hydroxyalkyl" means alkyl as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Methylenedioxy" means the radical —OCH$_2$O—.

"Sulfamoyl" means a group of formula —SO$_2$NR'R" wherein R' and R" each independently may be hydrogen or alkyl.

"Sulfonylamino" means a group of formula —NHR'—SO$^2$—R" wherein R' and R" each independently may be hydrogen or alkyl as defined herein.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Optionally substituted", when used in association with "aryl", phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Isomer" means different compounds that have the same molecular formula, but differ in the nature or the sequence of bonding of their atoms or in the arrangement of their atoms in space. Isomers that differ in the arrangement of their atoms in space are termed "stereoisomers". Stereoisomers that are mirror images of each other and optically active are termed "enantiomers", and stereoisomers that are not mirror images of one another are termed "diastereoisomers".

"Atropic isomer" means the isomers owing their existence to restricted rotation caused by hindrance of rotation of large groups about a central bond.

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog (Cahn et al., *Angew. Chem. Inter.* Edit. 1966, 5, 385; errata 511; Cahn et al., *Angew. Chem.* 1966, 78, 413; Cahn and Ingold *J. Chem. Soc.* (London) 1951, 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis- and trans-, or Z and E, which indicate that the groups are on the same or opposite side of the double bond in the molecule according to the Cahn-Ingold-Prelog rules.

"Leaving group" means the group with the meaning conventionally associated with it in synthetic organic chemistry, i.e., an atom or group displaceable under alkylating conditions. Examples of a leaving group include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" has the meaning conventionally associated with it in synthetic organic chemistry, i.e., a group which selectively blocks one reactive site in a multifunctional compound such that a chemical reaction can be carried out selectively at another unprotective reactive site. Certain processes of this invention rely upon the protecting groups to block reactive oxygen atoms present in the reactants. Acceptable protective groups for alcoholic or phenolic hydroxyl groups, which may be removed successively and selectively, include groups protected as acetates, haloalkyl carbonates, benzyl ethers, alkylsilyl ethers, heterocyclyl ethers, methyl or other alkyl ethers, and the like. Protective or blocking groups for carboxyl groups are similar to those described for hydroxyl groups, preferably tert-butyl, benzyl, or methyl esters. Examples of protecting groups can be found in T. W. Greene et al., *Protective Groups in Organic Chemistry,* 1999, J. Wiley, 2$^{nd}$ ed., and Harrison et al., *Compendium of Synthetic Organic Methods,* 1971–1996, Vols. 1–8, J. Wiley and Sons.

"Amino-protecting group" or "N-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyl-oxycarbonyl, p-nitrobenzyloxycarbonyl, tert-butoxycarbonyl (BOC), trifluoroacetyl, and the like.

"Deprotection" or "deprotecting" is the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxyde in alcoholic solutions, zinc in methanol, acetic acid, trifluoroacetic acid, palladium catalysts, or boron tribromide, and the like.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use or human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxy-ethanesulfonic acid, benzenesulfonic acid, 2-napthalenesulfonic acid, 4-methylbicyclo-[2.2.2]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methyl-glucamine, and the like. Acceptable inorganic bases include aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

"Pharmacological effect" as used herein encompasses effects produced in the subject that achieve the intended purpose of a therapy. In one preferred embodiment, a pharmacological effect means the treatment of a subject in need of such treatment. For example, a pharmacological effect would be one that results in the prevention, alleviation, or reduction of a disease state associated with pain, inflammation, urinary tract disease state, or asthma in a subject in need of such treatment. In a preferred embodiment, a pharmacological effect means that the activation of the IP receptors is associated with therapeutic benefit in a subject having a disease state treatable by the administration of an IP receptor modulator, in particular an IP receptor antagonist.

"Subject" means mammals and non-mammals. Examples of mammals include, but are not limited to, any member of the Mammalia class: humans, non-human primates such as chimpanzees and other apes and monkey species; farm animals such as cattle, horses, sheep, goats, swine; domestic animals such as rabbits, dogs and cats; laboratory animals including rodents, such as rats, mice, and guinea pigs, and the like. Examples of non-mammals include, but are not limited to birds, and the like. The term does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Treating" or "treatment" of a disease state includes:

(1) preventing the disease state, i.e., causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

Disease state" means any disease, disorder, condition, symptom, or indication.

"Disease state associated with the urinary tract" or "urinary tract disease state" or "uropathy" or "symptoms of the urinary tract", used interchangeably, means the pathologic changes in the urinary tract, or dysfunction of urinary bladder smooth muscle or its innervation causing disordered urinary storage or voiding. Symptoms of the urinary tract include (also known as detrusor hyperactivity), outlet obstruction, outlet insufficiency, and pelvic hypersensitivity.

"Outlet insufficiency" includes, but is not limited to, urethral hypermobility, intrinsic sphincteric deficiency, or mixed incontinence. It is usually symptomatically manifested as stress incontinence.

"Outlet obstruction" includes, but is not limited to, benign prostatic hypertrophy (BPH), urethral stricture disease, tumors, and the like. It is usually symptomatically manifested as obstructive (low flow rates, difficulty in initiating urination, and the like), and irritative (urgency, suprapubic pain, and the like).

"Overactive bladder" or "detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Pelvic Hypersensitivity" includes, but is not limited to, pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28$^{th}$ Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Modulator" means a molecule such as a compound that interacts with a target. The interactions include, but are not limited to, agonist, antagonist, and the like, as defined herein.

"Agonist" means a molecule such as a compound, a drug, an enzyme activator or a hormone that enhances the activity of another molecule or receptor site.

"Antagonist" means a molecule such as a compound, a drug, an enzyme inhibitor, or a hormone, that diminishes or prevents the action of another molecule or receptor site.

Nomenclature and Chemical Structures

In general, the nomenclature used in this Application is based on AutoNom®, a Beilstein Institute computerized system for the generation of IUPAC systematic nomenclature. Chemical structures shown herein were prepared using ISIS® version 2.2. Any open valency shown on a carbon, nitrogen or oxygen in the structures herein indicates the presence of a hydrogen.

As is well-known in the art, the imidazolin-2-ylamino group, in compounds such as the compounds of formula I, is in tautomeric equilibrium with the imidazolin-2-ylideneamino group:

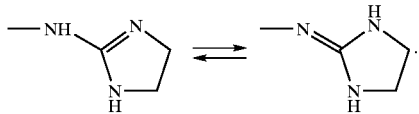

For convenience, all the compounds of formula I are shown as having the imidazolin-2-ylamino structure, but it is to be understood that compounds of both tautomeric forms are intended to be within the scope of the invention.

Compounds

The invention provides compounds of the formula I:

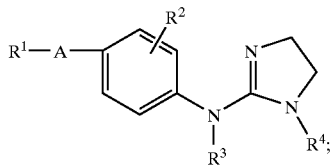

wherein:
- $R^1$ is optionally substituted aryl or optionally substituted heteroaryl;
- $R^2$ is hydrogen, alkyl, alkoxy, haloalkyl or halogen;
- $R^3$ and $R^4$ each independently is hydrogen or alkoxycarbonyl;
- A is —C(O)—NR$^a$—(CR$^b$R$^c$)$_n$— or —NR$^a$—C(O)—(CR$^b$R$^c$)$_n$—;
- n is from 1 to 6;
- $R^a$ is hydrogen, alkyl or cycloalkyl; and
- $R^b$ and $R^c$ each independently is hydrogen or alkyl;

or a pharmaceutically acceptable salt, solvate or prodrug thereof.

Where any of $R^2$, $R^3$, $R^a$, $R^b$ and $R^c$ is alkyl, or contains an alkyl moiety, and where $R^1$ contains an alkyl moiety, such alkyl is preferably lower alkyl, i.e. $C_1$–$C_6$alkyl, and more preferably $C_1$–$C_4$alkyl.

By way of example, and not of limitation, the aryl or heteroaryl $R^1$ may be optionally substituted by one, two, or three substituents independently selected from alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino. In certain embodiments $R^1$ is phenyl optionally substituted with alkyl, alkoxy, alkenyl, optionally substituted phenyl, optionally substituted heteroaryl, optionally substituted heterocyclyl, haloalkyl, alkoxy, nitro, cyano, or halogen.

In certain embodiments $R^1$ is 4-alkoxyphenyl. The 4-alkoxyphenyl may be 4-methoxyphenyl, 4-ethoxyphenyl, 4-propoxyphenyl, 4-isopropoxyphenyl, 4-butoxyphenyl or 4-isobutoxyphenyl.

In certain embodiments $R^1$ is 4-alkylphenyl. The 4-alkyl phenyl may be 4-methylphenyl, 4-ethylphenyl, 4-propylphenyl, 4-isopropylphenyl, 4-butykphenyl or 4-isobutylphenyl.

In certain embodiments $R^1$ is aryloxyphenyl such as 4-phenoxyphenyl.

In certain embodiments $R^1$ is 4-cycloalkyloxyphenyl. The compound 4-cycloalkyloxyphenyl may be 4-cyclopentyloxyphenyl or 4-cycloheptyloxyphenyl.

In certain embodiments $R^1$ is 4-cycloalkylalkoxyphenyl, such as cyclopropylmethoxyphenyl.

In certain embodiments $R^1$ is 4-alkoxyalkyloxyphenyl, such as 4-(2-methoxyethyloxy)-phenyl.

In certain embodiments $R^1$ is 4-hydroxyalkyloxyphenyl. The 4-hydroxyalkyloxyphenyl may be 4-(2-hydroxyethyloxy)-phenyl, 4-(2,3-dihydroxypropyloxy)-phenyl or 4-(3-hydroxy-2-hydroxymethyl-propyloxy)-phenyl.

In certain embodiments $R^1$ is 4-dialkylaminophenyl such as 4-(N,N-diethylamino)-phenyl.

In certain embodiments $R^1$ is 4-halophenyl, such as 4-fluorophenyl, 4-chlorophenyl or 4-bromophenyl.

In certain embodiments $R^1$ is optionally substituted 4-biphenyl. The optionally substituted 4-biphenyl may be 4'-fluoro-4-biphenyl, 4'-metnoxy-4-biphenyl, 4'-methyl-4-biphenyl, 4'-chloro-4-biphenyl or 4-biphenyl.

In certain embodiments $R^1$ is 4-cyanophenyl.

In certain embodiments $R^1$ is 4-alkenylphenyl such as 4-vinyl-phenyl.

In certain embodiments $R^1$ is 4-cycloalkylphenyl, such as 4-cyclohexylphenyl.

In certain embodiments $R^1$ is optionally substituted 4-benzyloxyphenyl.

In certain embodiments $R^1$ is 4-dialkylsulfamoylphenyl such as 4-diethylsulfamoylphenyl or 4-dimethylsulfamoylphenyl.

In certain embodiments $R^1$ is 4-alkylsulfamoylphenyl such as 4-ethylsulfamoylphenyl.

In certain embodiments $R^1$ is 4-heteroarylphenyl wherein the heteroaryl moiety is optionally substituted. The 4-heteroarylphenyl may be, for example, optionally substituted pyrazolyl, optionally substituted pyrimidinyl or optionally substituted thiophenyl. In specific embodiments, the 4-heteroarylphenyl may be optionally substituted 4-(4-methyl-pyrazol-1-yl)-phenyl, 4-(3-methyl-pyrazol-1-yl)-phenyl, 4-pyrazol-1-yl-phenyl, 4-thiophen-3-yl-phenyl, 4-pyrimidin-2-yl-phenyl or 4-(2-chloro-thiophen-3-yl)-phenyl.

In certain embodiments $R^1$ is 4-heterocyclylphenyl wherein the heterocyclyl moiety is optionally substituted. The 4-heterocycylphenyl may be morpholinylphenyl, thiomorpholinylphenyl, 1,1-dioxythiomorpholinylphenyl, optionally substituted piperazinylphenyl or optionally substituted piperidinylphenyl. In specific embodiments the 4-heterocycylphenyl may be 4-morpholin-4-yl-phenyl, 4-(4-carboxylate ester piperazin-1-yl)-phenyl, 4-(4-ethanesulfonyl-piperazin-1-yl)-phenyl, 4-(4-propane-2-sulfonyl-piperazin-1-yl)-phenyl, 4-(4-methanesulfonyl-piperazin-1-yl)-phenyl, 4-(4-methyl-piperazin-1-yl)-phenyl, 4-(4-ethyl-piperazin-1-yl)-phenyl, 4-(4-methoxypiperidin-1-yl, 4-(8-aza-spiro[4.5]dec-8-yl)-phenyl, 4-piperazin-1-yl-phenyl, 4-methyl-piperidin-1-yl-phenyl, 4-pyrrolidin-1-yl-phenyl, 4-hydroxy-piperidine-1-yl-phenyl or 4-piperidin-1-ylphenyl.

In certain embodiments $R^1$ is 4-heterocycyloxyphenyl wherein the heterocyclyl moiety is optionally substituted. The 4-heterocycyloxyphenyl may be tetrahydropyranyloxyphenyl or optionally substituted piperidin-4-yloxy-phenyl. In specific embodiments the 4-heterocycyloxyphenyl may be 4-(tetrahydropyran-4-yloxy)-phenyl, 4-(piperidin-4-yloxy)-phenyl, 4-(1-ethyl-piperidin-4-yloxy)-phenyl or 4-(1-carboxylate ethyl ester-piperidin-4-yloxy)-phenyl.

In certain embodiments $R^1$ is 4-heterocycylalkyloxyphenyl wherein the heterocyclyl moiety is optionally substituted. The 4-heterocycylalkyloxyphenyl may be tetrahydropyranylmethoxyphenyl or optionally substituted piperidinylmethyloxyphenyl. In specific embodiments the 4-heterocycylalkyloxyphenyl may be 4-(tetrahydropyran-2-ylmethoxy)-phenyl, 4-(piperidin-4-ylmethoxy)-phenyl, 4-(1-[ethyl carbamoyl]-piperidin-4-ylmethoxy)-phenyl, 4-(1-methanesulfonyl-piperidin-4-ylmethoxy)-phenyl, 4-(1-carboxylate ethyl ester-piperidin-4-ylmethoxy)-phenyl, 4-(1-methyl-piperidin-4-ylmethoxy)-phenyl or 4-(1-ethyl-piperidin-4-ylmethoxy)-phenyl.

In certain embodiments $R^1$ is 4-heterocycylsulfonylphenyl wherein the heterocyclyl moiety is optionally substituted. The 4-heterocycylsulfonylphenyl may be morpholinylsulfonylphenyl, thiomorpholinylsulfonylphenyl, 1,1-dioxythiomorpholinylsulfonylphenyl, optionally substituted piperazinylsulfonylphenyl or optionally substituted piperidinylsulfonylphenyl. In specific embodiments the 4-heterocycylsulfonylphenyl may be 4-(morpholin-4-sulfonyl)-phenyl, 4-(4-methyl-piperazine-1-sulfonyl)-phenyl, 4-(piperidin-1-sulfonyl)-phenyl or 4-(4-methyl-piperidin-1-sulfonyl)-phenyl.

In embodiments of the invention wherein $R^1$ is optionally substituted phenyl, the compounds of the invention fall more specifically within the formula II:

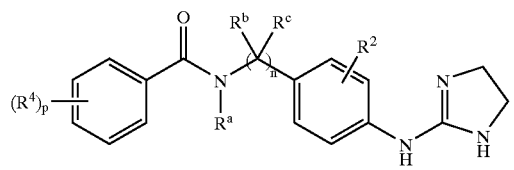

II wherein:
p is from 0 to 4;
$R^4$ is alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino.

$R^a$, $R^b$ and $R^c$ each independently is hydrogen, alkyl or cycloalkyl; preferably $R^b$ and $R^c$ are hydrogen; and n and $R^2$ are as defined above. More preferably, p is 0 or 1.

Where any of $R^4$, $R^a$, $R^b$ and $R^c$ are alkyl or contain an alkyl moiety, such alkyl is preferably lower alkyl, i.e. $C_1$–$C_6$alkyl, and more preferably $C_1$–$C_4$alkyl.

In other embodiments the subject compounds may be of the formula III:

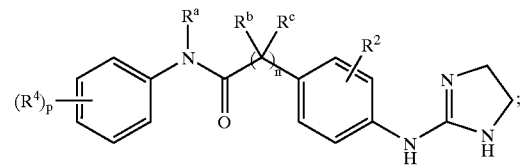

III wherein n, p, $R^2$, $R^4$, $R^a$, $R^b$ and $R^c$ are as defined above.

In certain embodiments, the compounds of the invention may be of the formula IV:

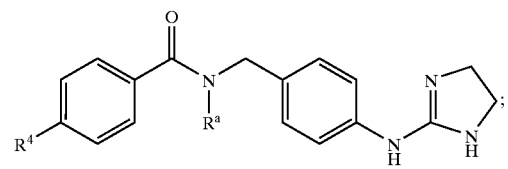

IV wherein $R^4$ and $R^a$ are as defined above.

In certain embodiments of formula IV, $R^a$ may be hydrogen, alkyl or cyclopropyl.

In certain embodiments of formula IV, $R^4$ may be alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino.

In embodiments wherein $R^4$ is alkoxy, the alkoxy may be methoxy, ethoxy, propoxy, isopropoxy, butoxy or isobutoxy.

In embodiments wherein $R^4$ is alkyl, the alkyl may be methyl, ethyl, propyl, isopropyl, butyl or isobutyl.

In embodiments wherein $R^4$ is aryloxy, $R^4$ may be phenoxy.

In embodiments wherein $R^4$ is cycloalkyloxy. The compound cycloalkyloxy may be cyclopentyloxy or cycloheptyloxy.

In embodiments wherein $R^4$ is cycloalkylalkoxy, $R^4$ may be cyclopropylmethoxy.

In embodiments wherein $R^4$ is alkoxyalkyloxy, $R^4$ may be 2-methoxyethyloxy.

In embodiments wherein $R^4$ is hydroxyalkyloxy, $R^4$ may be 2-hydroxyethyloxy, 2,3-dihydroxypropyloxy or 3-hydroxy-2-hydroxymethyl-propyloxy.

In embodiments wherein $R^4$ is dialkylamino $R^4$ may be N,N-diethylamino.

In embodiments wherein $R^4$ is halo, $R^4$ may be fluoro, chloro or bromo.

In embodiments wherein $R^4$ is optionally substituted phenyl, the optionally substituted phenyl may be 4-fluorophenyl, 4-methoxyphenyl, 4-methylphenyl, 4-chlorophenyl or phenyl.

In certain embodiments $R^4$ may be cyano.
In certain embodiments $R^4$ may be alkenyl, such as vinyl.
In certain embodiments $R^4$ may be cycloalkyl, such as cyclohexyl.

In embodiments wherein R⁴ is optionally substituted aryloxy, R⁴ may be benzyloxy.

In certain embodiments R⁴ may be dialkylsulfamoyl such as diethylsulfamoyl or dimethylsulfamoyl.

In certain embodiments R⁴ may be alkylsulfamoyl, such as ethylsulfamoyl.

In certain embodiments R⁴ is heteroaryl wherein the heteroaryl moiety is optionally substituted, such as, for example, optionally substituted pyrazolyl, optionally substituted pyrimidinyl or optionally substituted thiophenyl. In specific embodiments, R⁴ may be optionally substituted methyl-pyrazol-1-yl, 3-methyl-pyrazol-1-yl, pyrazol-1-yl, thiophen-3-yl, pyrimidin-2-yl or 2-chloro-thiophen-3-yl.

In certain embodiments R⁴ is heterocyclyl wherein the heterocyclyl moiety is optionally substituted, such as morpholinyl, thiomorpholinyl, 1,1-dioxythiomorpholinyl, optionally substituted piperazinyl or optionally substituted piperidinyl. In specific embodiments R⁴ may be morpholinyl, carboxylate ester piperazin-1-yl, ethanesulfonyl-piperazin-1-yl, propane-2-sulfonyl-piperazin-1-yl, methanesulfonyl-piperazin-1-yl, methylpiperazin-1-yl, ethyl-piperazin-1-yl, methoxypiperidin-1-yl, 8-aza-spiro [4.5]dec-8-yl, piperazin-1-yl, methyl-piperidin-1-yl, pyrrolidin-1-yl, hydroxy-piperidine-1-yl or piperidin-1-yl.

In certain embodiments R⁴ is heterocycyloxy wherein the heterocyclyl moiety is optionally substituted, such as optionally substituted tetrahydropyranyloxy or optionally substituted piperidin-yloxy-. In specific embodiments R⁴ may be tetrahydropyran-yloxy, piperidin-yloxy, 1-ethyl-piperidin-yloxy or 1-carboxylate ethyl ester-piperidin-yloxy.

In certain embodiments R⁴ is heterocycylalkyloxy wherein the heterocyclyl moiety is optionally substituted, such as optionally substituted tetrahydropyranylmethoxy or optionally substituted piperidinylmethyloxy. In specific embodiments R⁴ may be tetrahydropyran-2-ylmethoxy, piperidin-ylmethoxy, 1-[ethyl carbamoyl]-piperidin-ylmethoxy, 1-methanesulfonyl-piperidin-ylmethoxy, 1-carboxylate ethyl ester-piperidin-ylmethoxy, 1-methyl-piperidin-ylmethoxy or 1-ethyl-piperidin-ylmethoxy.

In certain embodiments R⁴ is heterocyclylsulfonyl wherein the heterocyclyl moiety is optionally substituted, such as optionally substituted morpholinylsulfonyl, optionally substituted thiomorpholinyl, optionally substituted 1,1-dioxythiomorpholinyl, optionally substituted piperazinylsulfonyl or optionally substituted piperidinylsulfonyl. In specific embodiments R⁴ may be morpholin-sulfonyl, methyl-piperazine-1-sulfonyl, piperidin-1-sulfonyl or methyl-piperidin-1-sulfonyl.

Representative compounds in accordance with the invention are shown in Table 1.

TABLE 1

| # | Structure | Name (Autonom ™) | M + H |
|---|---|---|---|
| 1 | 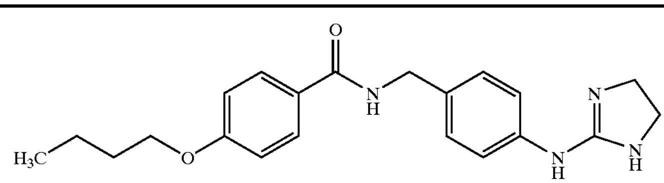 | 4-Butoxy-N-[4-(4,5-dihydro-1H-imidazol-2-ylamino)-benzyl]-benzamide | 367 |
| 2 | 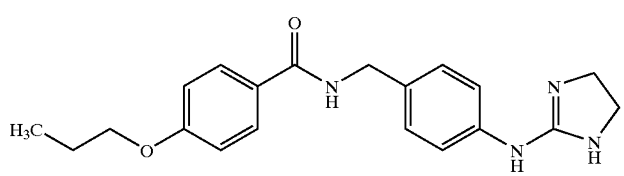 | N-[4-(4,5-Dihydro-1H-imidazol-2-ylamino)-benzyl]-4-propoxy-benzamide | 353 |
| 3 | 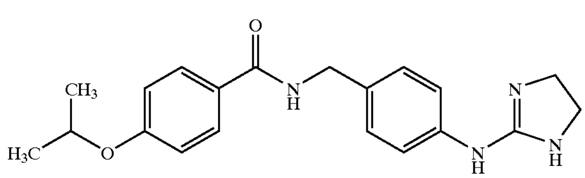 | N-[4-(4,5-Dihydro-1H-imidazol-2-ylamino)-benzyl]-4-isopropoxy-benzamide | 353 |
| 4 | 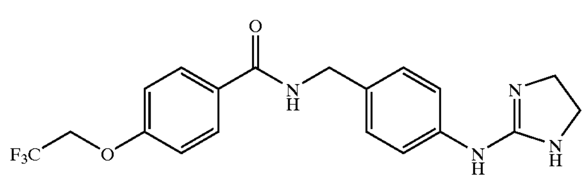 | N-[4-(4,5-Dihydro-1H-imidazol-2-ylamino)-benzyl]-4-(2,2,2-tri-fluoroethoxy)-benzamide | 379 |
| 5 | 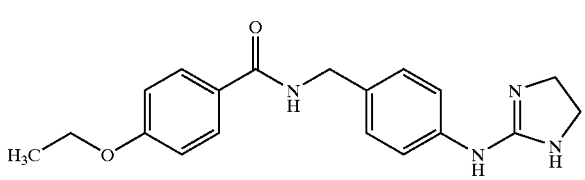 | N-[4-(4,5-Dihydro-1H-imidazol-2-ylamino)-benzyl]-4-ethoxy-benzamide | 339 |

TABLE 1-continued

| # | Structure | Name (Autonom™) | M + H |
|---|---|---|---|
| 6 | 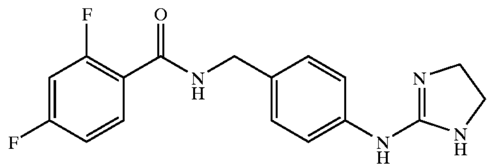 | N-[4-(4,5-Dihydro-1H-imidazol-2-ylamino)-benzyl]-2,4-difluoro-benzamide | 331 |
| 7 | 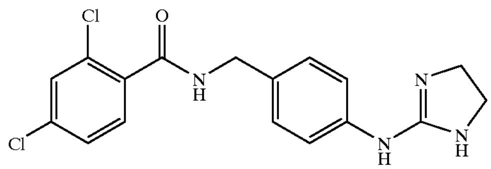 | 2,4-Dichloro-N-[4-(4,5-dihydro-1H-imidazol-2-ylamino)-benzyl]-benzamide | 364 |
| 8 | 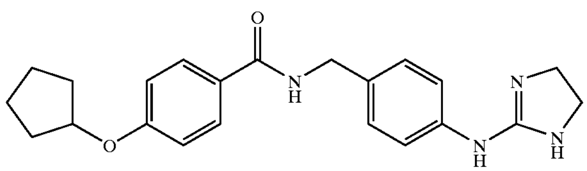 | 4-Cyclopentyloxy-N-[4-(4,5-dihydro-1H-imidazol-2-ylamino)-benzyl]-benzamide | 379 |
| 9 | 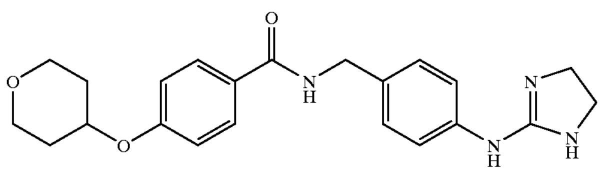 | N-[4-(4,5-Dihydro-1H-imidazol-2-ylamino)-benzyl]-4-(tetrahydro-pyran-4-yloxy)-benzamide | 395 |
| 10 | 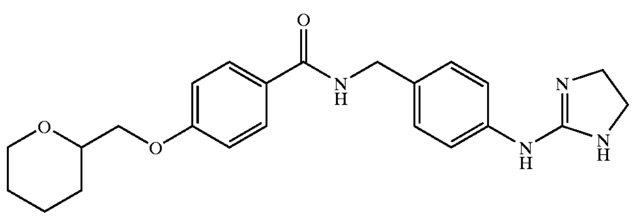 | N-[4-(4,5-Dihydro-1H-imidazol-2-ylamino)-benzyl]-4-(tetrahydro-pyran-2-ylmethoxy)-benzamide | 409 |
| 11 | 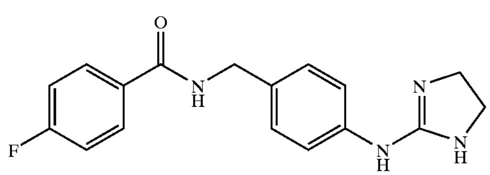 | N-[4-(4,5-Dihydro-1H-imidazol-2-ylamino)-benzyl]-4-fluoro-benzamide | 313 |
| 12 | 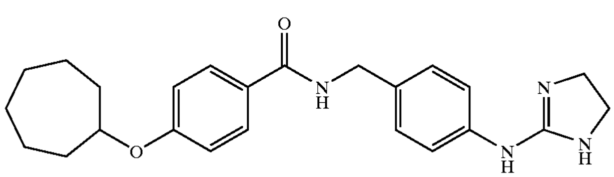 | 4-Cycloheptyloxy-N-[4-(4,5-dihydro-1H-imidazol-2-ylamino)-benzyl]-benzamide | 408 |
| 13 | 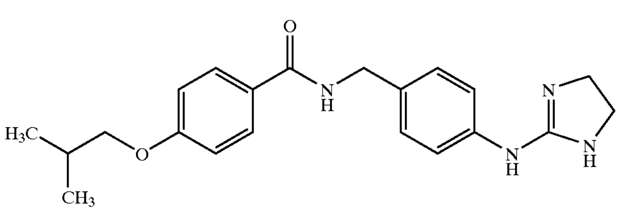 | N-[4-(4,5-Dihydro-1H-imidazol-2-ylamino)-benzyl]-4-isobutoxy-benzamide | 367 |

TABLE 1-continued

| # | Name (Autonom ™) | M + H |
|---|---|---|
| 14 | N-[4-(4,5-Dihydro-1H-imidazol-2-ylamino)-benzyl]-4-(tetrahydro-pyran-4-ylmethoxy)-benzamide | 409 |
| 15 | 4-Cyclopropylmethoxy-N-[4-(4,5-dihydro-1H-imidazol-2-ylamino)-benzyl]-benzamide | 365 |
| 16 | N-[4-(4,5-Dihydro-1H-imidazol-2-ylamino)-benzyl]-4-(2-methoxy-ethoxy)-benzamide | 369 |
| 17 | N-[4-(4,5-Dihydro-1H-imidazol-2-ylamino)-benzyl]-4-dimethylamino-benzamide | 338 |
| 18 | N-[4-(4,5-Dihydro-1H-imidazol-2-ylamino)-benzyl]-4-methylamino-benzamide | 324 |
| 19 | N-[4-(4,5-Dihydro-1H-imidazol-2-ylamino)-benzyl]-4-(piperidin-4-ylmethoxy)-benzamide | 409 |
| 20 | 4-Chloro-N-[4-(4,5-dihydro-1H-imidazol-2-ylamino)-benzyl]-benzamide | 330 |

TABLE 1-continued

| # | Structure | Name (Autonom ™) | M + H |
|---|---|---|---|
| 21 | 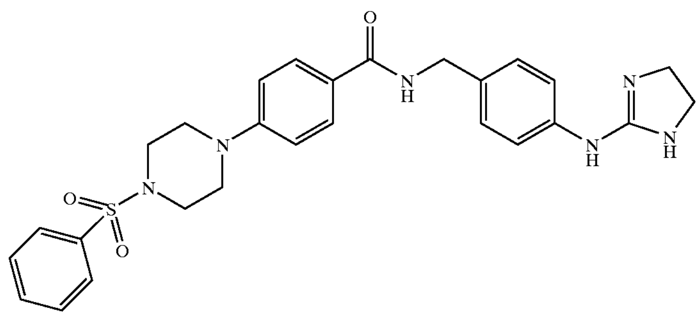 | 4-(4-Benzenesulfonyl-piperazin-1-yl)-N-[4-(4,5-dihydro-1H-imidazol-2-ylamino)-benzyl]-benzamide | 520 |
| 22 | 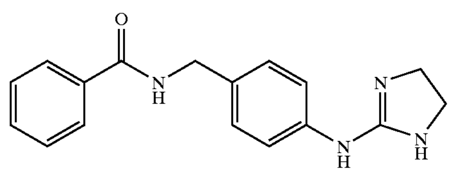 | N-[4-(4,5-Dihydro-1H-imidazol-2-ylamino)-benzyl]-benzamide | 295 |
| 23 | 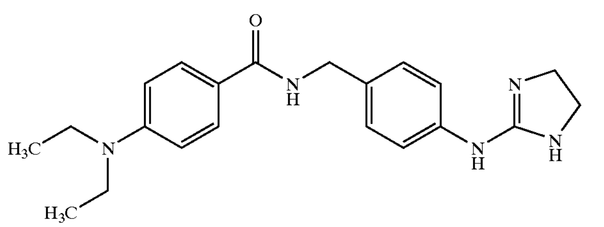 | 4-Diethylamino-N-[4-(4,5-dihydro-1H-imidazol-2-ylamino)-benzyl]-benzamide | 366 |
| 24 | 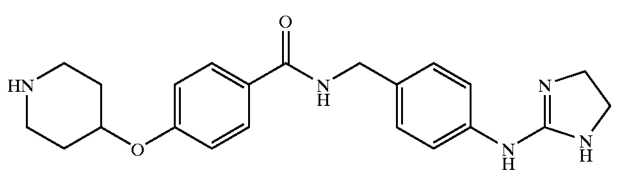 | N-[4-(4,5-Dihydro-1H-imidazol-2-ylamino)-benzyl]-4-(piperidin-4-yl-oxy)-benzamide | 394 |
| 25 | 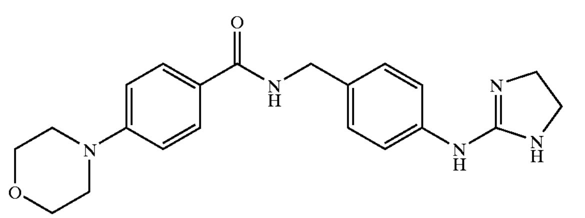 | N-[4-(4,5-Dihydro-1H-imidazol-2-ylamino)-benzyl]-4-morpholin-4-yl-benzamide | 380 |
| 26 | 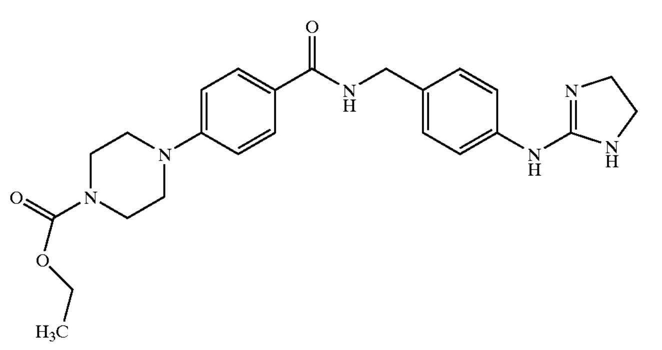 | 4-{4-[4-(4,5-Dihydro-1H-imidazol-2-ylamino)-benzyl-carbamoyl]-phenyl}-piperazine-1-carboxylic acid ethyl ester | 452 |

TABLE 1-continued

| # | Structure | Name (Autonom ™) | M + H |
|---|---|---|---|
| 27 | 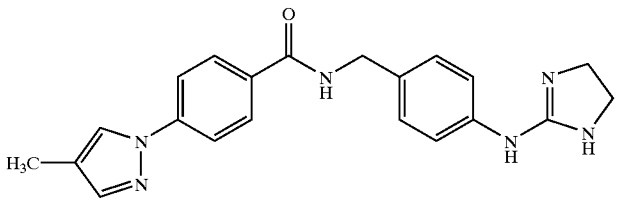 | N-[4-(4,5-Dihydro-1H-imidazol-2-ylamino)-benzyl]-4-(4-methyl-pyrazol-1-yl)-benzamide | 375 |
| 28 | 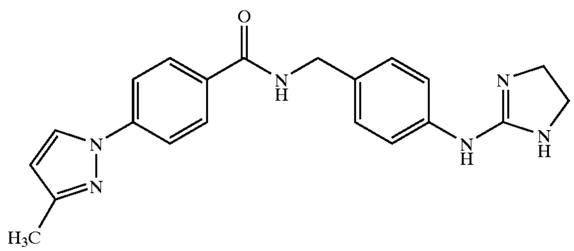 | N-[4-(4,5-Dihydro-1H-imidazol-2-ylamino)-benzyl]-4-(3-methyl-pyrazol-1-yl)-benzamide | 375 |
| 29 | 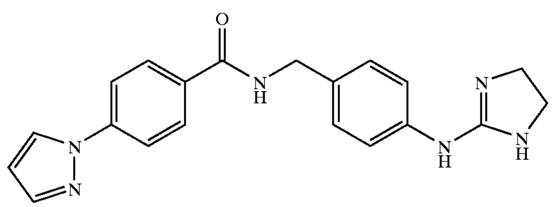 | N-[4-(4,5-Dihydro-1H-imidazol-2-ylamino)-benzyl]-4-pyrazol-1-yl-benzamide | 361 |
| 30 | 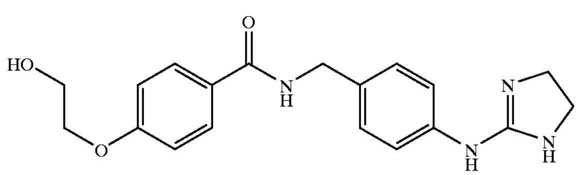 | N-[4-(4,5-Dihydro-1H-imidazol-2-ylamino)-benzyl]-4-(2-hydroxy-ethoxy)-benzamide | 355 |
| 31 | 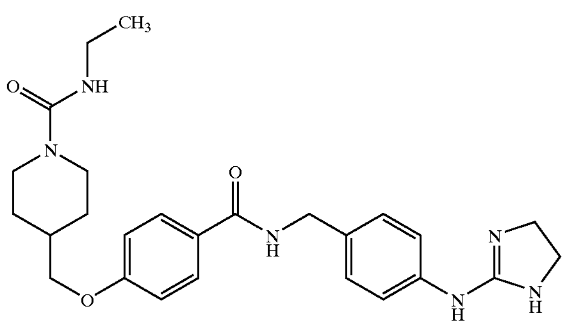 | 4-{4-[4-(4,5-Dihydro-1H-imidazol-2-ylamino)-benzyl-carbamoyl]-phenoxymethyl}-piperidine-1-carboxylic acid ethylamide | 480 |
| 32 | 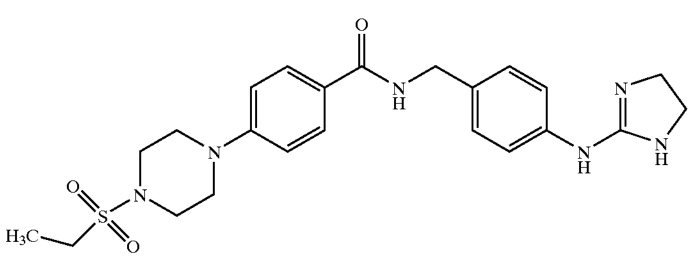 | N-[4-(4,5-Dihydro-1H-imidazol-2-ylamino)-benzyl]-4-(4-ethanesulfonyl-piperazin-1-yl)-benzamide | 472 |

TABLE 1-continued

| # | Structure | Name (Autonom ™) | M + H |
|---|---|---|---|
| 33 | 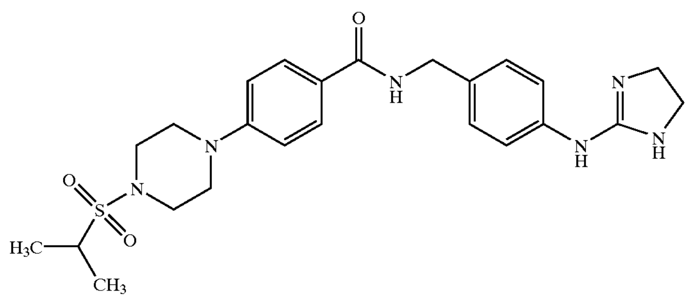 | N-[4-(4,5-Dihydro-1H-imidazol-2-ylamino)-benzyl]-4-[4-(propane-2-sulfonyl)-piperazin-1-yl]-benzamide | 486 |
| 34 | 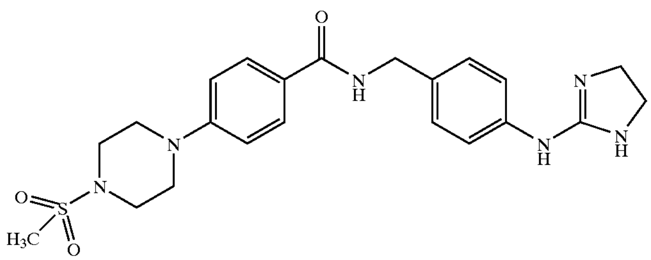 | N-[4-(4,5-Dihydro-1H-imidazol-2-ylamino)-benzyl]-4-(4-methanesulfonyl-piperazin-1-yl)-benzamide | 458 |
| 35 | 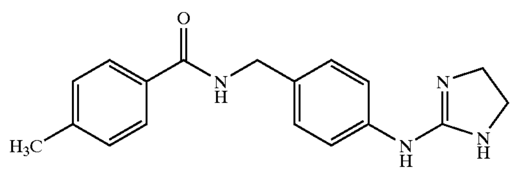 | N-[4-(4,5-Dihydro-1H-imidazol-2-ylamino)-benzyl]-4-methyl-benzamide | 309 |
| 36 | 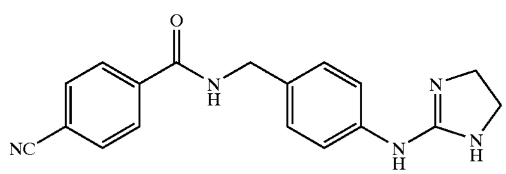 | 4-Cyano-N-[4-(4,5-dihydro-1H-imidazol-2-ylamino)-benzyl]-benzamide | 320 |
| 37 | 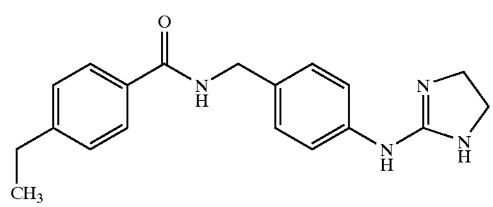 | N-[4-(4,5-Dihydro-1H-imidazol-2-ylamino)-benzyl]-4-ethyl-benzamide | 323 |
| 38 | 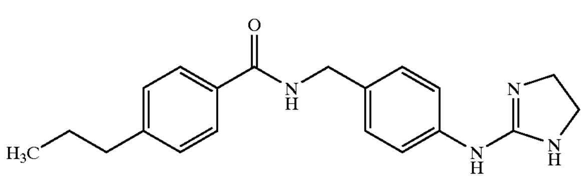 | N-[4-(4,5-Dihydro-1H-imidazol-2-ylamino)-benzyl]-4-propyl-benzamide | 337 |
| 39 | 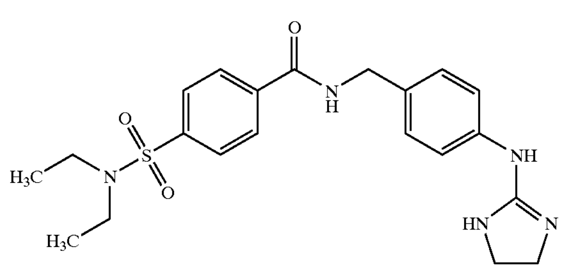 | 4-Diethylsulfamoyl-N-[4-(4,5-dihydro-1H-imidazol-2-ylamino)-benzyl]-benzamide | 430 |

TABLE 1-continued

| # | Structure | Name (Autonom ™) | M + H |
|---|---|---|---|
| 40 | 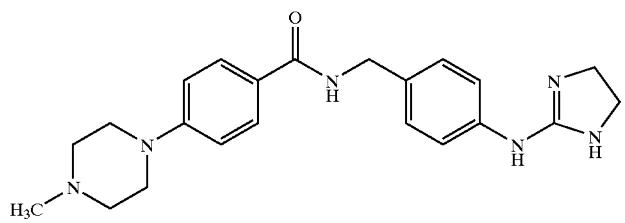 | N-[4-(4,5-Dihydro-1H-imidazol-2-ylamino)-benzyl]-4-(4-methyl-piperazin-1-yl)-benzamide | 394 |
| 41 | 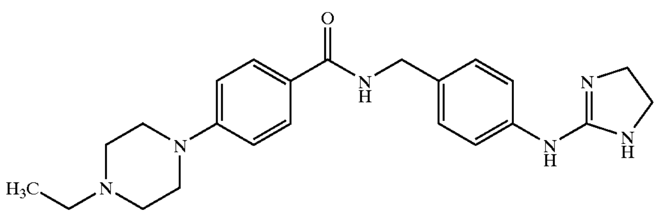 | N-[4-(4,5-Dihydro-1H-imidazol-2-ylamino)-benzyl]-4-(4-ethyl-piperazin-1-yl)-benzamide | 408 |
| 42 | 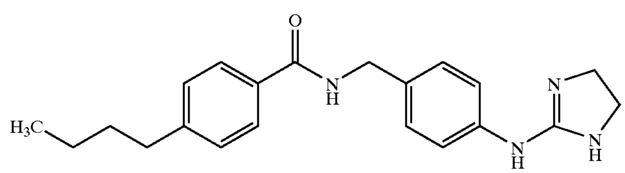 | 4-Butyl-N-[4-(4,5-dihydro-1H-imidazol-2-ylamino)-benzyl]-benzamide | 351 |
| 43 | 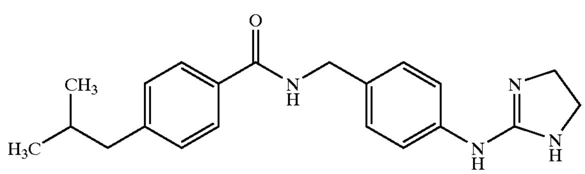 | N-[4-(4,5-Dihydro-1H-imidazol-2-ylamino)-benzyl]-4-isobutyl-benzamide | 351 |
| 44 | 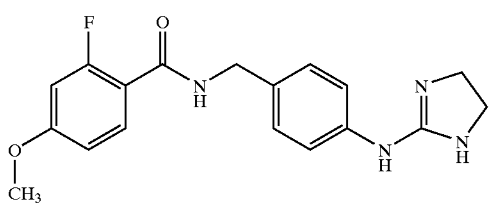 | N-[4-(4,5-Dihydro-1H-imidazol-2-ylamino)-benzyl]-2-fluoro-4-methoxy-benzamide | 344 |
| 45 | 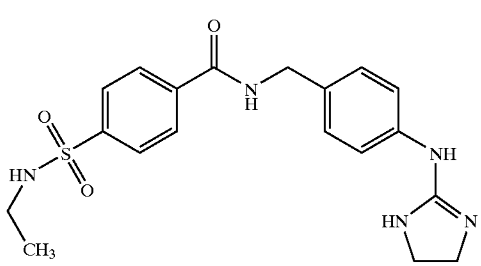 | N-[4-(4,5-Dihydro-1H-imidazol-2-ylamino)-benzyl]-4-ethylsulfamoyl-benzamide | 402 |
| 46 | 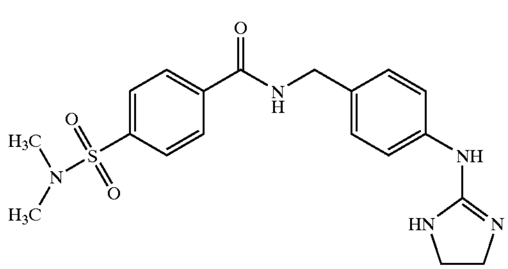 | N-[4-(4,5-Dihydro-1H-imidazol-2-ylamino)-benzyl]-4-di-methylsulfamoyl-benzamide | 402 |

TABLE 1-continued

| # | Structure | Name (Autonom ™) | M + H |
|---|-----------|------------------|-------|
| 47 | 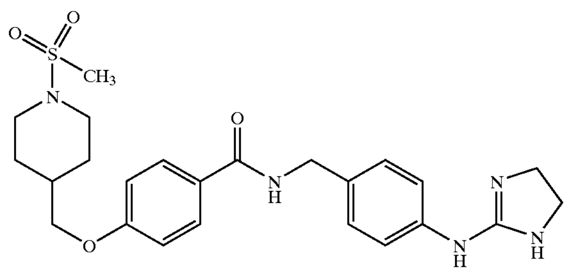 | N-[4-(4,5-Dihydro-1H-imidazol-2-ylamino)-benzyl]-4-(1-methanesulfonyl-piperidin-4-ylmethoxy)-benzamide | 487 |
| 48 | 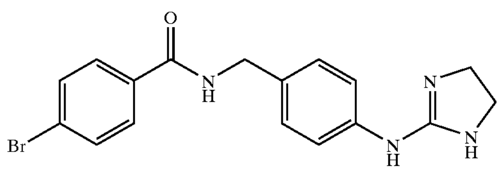 | 4-Bromo-N-[4-(4,5-dihydro-1H-imidazol-2-ylamino)-benzyl]-benzamide | 374 |
| 49 | 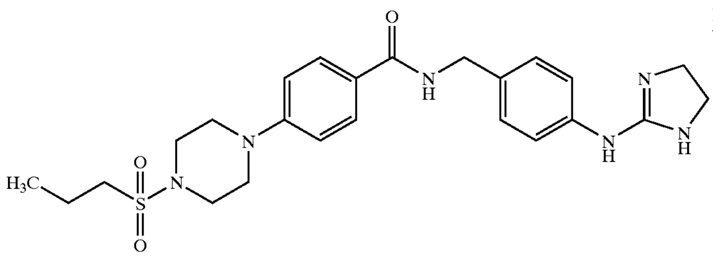 | N-[4-(4,5-Dihydro-1H-imidazol-2-ylamino)-benzyl]-4-[4-(propane-1-sulfonyl)-piperazin-1-yl]-benzamide | 486 |
| 50 | 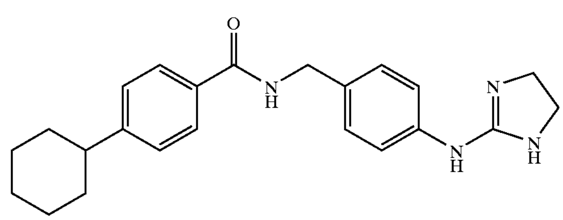 | 4-Cyclohexyl-N-[4-(4,5-dihydro-1H-imidazol-2-ylamino)-benzyl]-benzamide | 378 |
| 51 | 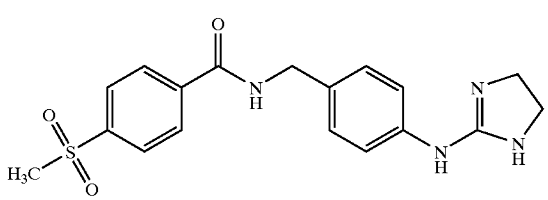 | N-[4-(4,5-Dihydro-1H-imidazol-2-ylamino)-benzyl]-4-methanesulfonyl-benzamide | 373 |
| 52 | 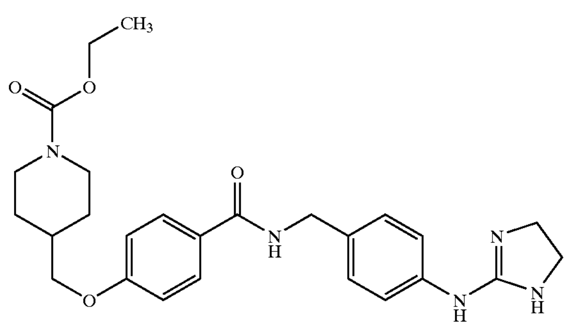 | 4-{4-[4-(4,5-Dihydro-1H-imidazol-2-ylamino)-benzylcarbamoyl]-phenoxy-methyl}-piperidine-1-carboxylic acid ethyl ester | 481 |

TABLE 1-continued

| # | Structure | Name (Autonom ™) | M + H |
|---|---|---|---|
| 53 | 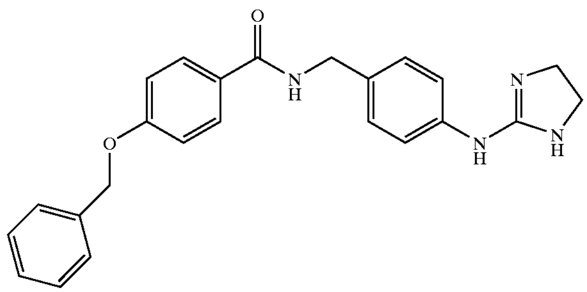 | 4-Benzyloxy-N-[4-(4,5-dihydro-1H-imidazol-2-ylamino)-benzyl]-benzamide | 401 |
| 54 | 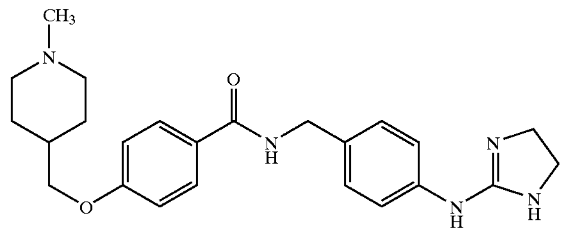 | N-[4-(4,5-Dihydro-1H-imidazol-2-ylamino)-benzyl]-4-(1-methyl-piperidin-4-ylmethoxy)-benzamide | 423 |
| 55 | 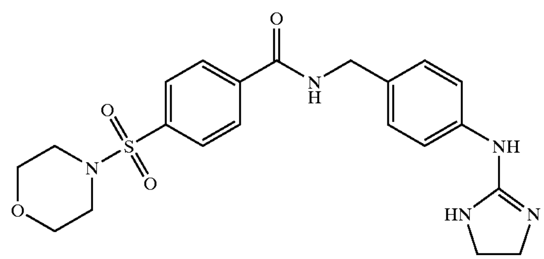 | N-[4-(4,5-Dihydro-1H-imidazol-2-ylamino)-benzyl]-4-(morpholine-4-sulfonyl)-benzamide | 445 |
| 56 | 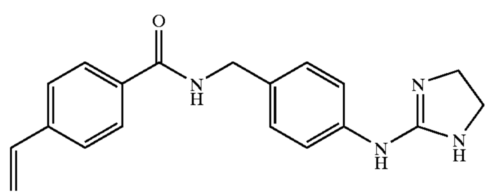 | N-[4-(4,5-Dihydro-1H-imidazol-2-ylamino)-benzyl]-4-vinyl-benzamide | 321 |
| 57 | 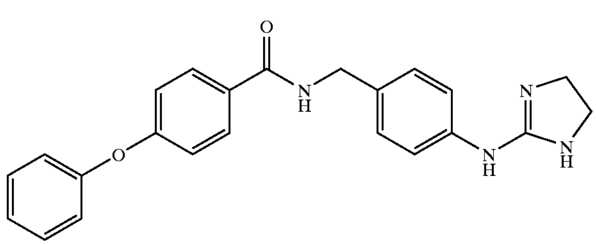 | N-[4-(4,5-Dihydro-1H-imidazol-2-ylamino)-benzyl]-4-phenoxy-benzamide | 387 |
| 58 | 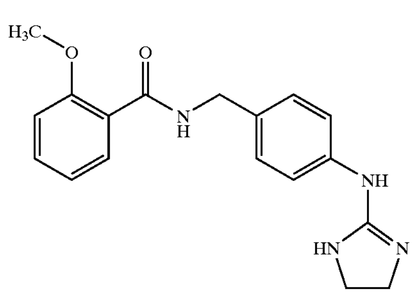 | N-[4-(4,5-Dihydro-1H-imidazol-2-ylamino)-benzyl]-2-methoxy-benzamide | 325 |

TABLE 1-continued

| # | Structure | Name (Autonom ™) | M + H |
|---|---|---|---|
| 59 | 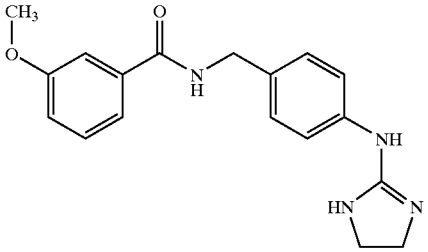 | N-[4-(4,5-Dihydro-1H-imidazol-2-ylamino)-benzyl]-3-methoxy-benzamide | 325 |
| 60 | 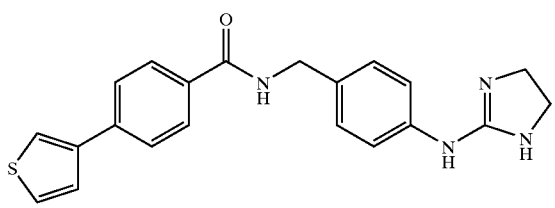 | N-[4-(4,5-Dihydro-1H-imidazol-2-ylamino)-benzyl]-4-thiophen-3-yl-benzamide | 377 |
| 61 | 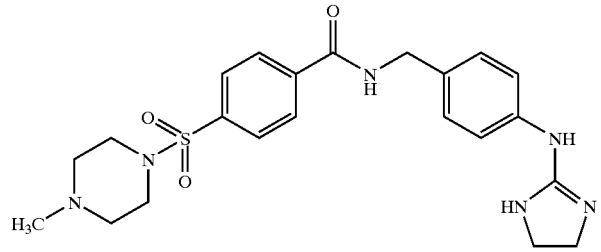 | N-[4-(4,5-Dihydro-1H-imidazol-2-ylamino)-benzyl]-4-(4-methyl-piperazine-1-sulfonyl)-benzamide | 458 |
| 62 | 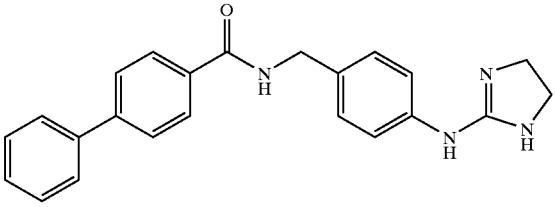 | Biphenyl-4-carboxylic acid 4-(4,5-dihydro-1H-imidazol-2-ylamino)-benzylamide | 371 |
| 63 | 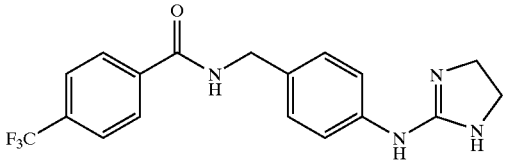 | N-[4-(4,5-Dihydro-1H-imidazol-2-ylamino)-benzyl]-4-trifluoromethyl-benzamide | 363 |
| 64 | 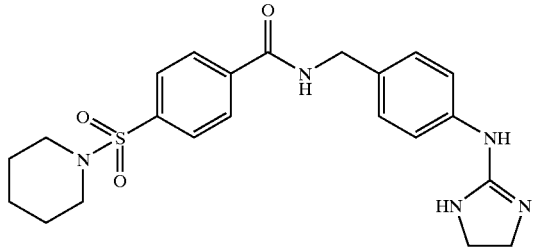 | N-[4-(4,5-Dihydro-1H-imidazol-2-ylamino)-benzyl]-4-(piperidine-1-sulfonyl)-benzamide | 443 |

TABLE 1-continued

| # | Structure | Name (Autonom ™) | M + H |
|---|---|---|---|
| 65 | 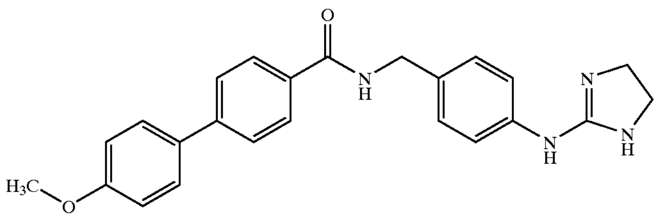 | 4'-Methoxy-biphenyl-4-carboxylic acid 4-(4,5-dihydro-1H-imidazol-2-ylamino)-benzylamide | 401 |
| 66 | 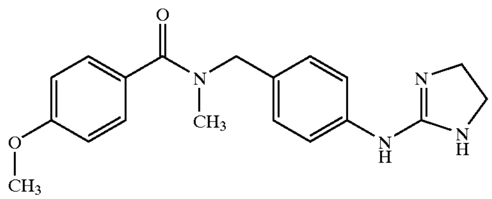 | N-[4-(4,5-Dihydro-1H-imidazol-2-ylamino)-benzyl]-4-methoxy-N-methyl-benzamide | 341 |
| 67 | 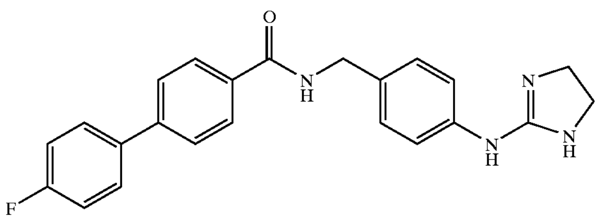 | 4'-Fluoro-biphenyl-4-carboxylic acid 4-(4,5-dihydro-1H-imidazol-2-ylamino)-benzylamide | 389 |
| 68 | 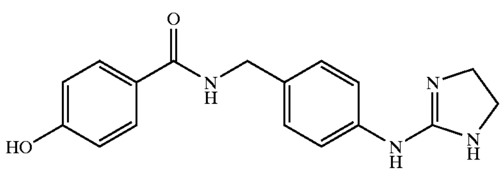 | N-[4-(4,5-Dihydro-1H-imidazol-2-ylamino)-benzyl]-4-hydroxy-benzamide | 311 |
| 69 | 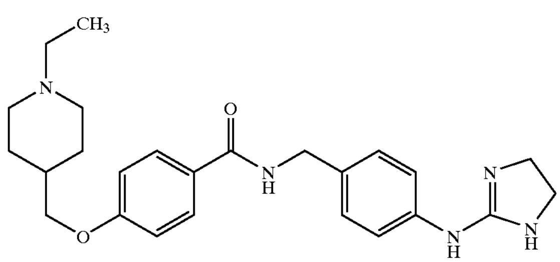 | N-[4-(4,5-Dihydro-1H-imidazol-2-ylamino)-benzyl]-4-(1-ethyl-piperidin-4-ylmethoxy)-benzamide | 437 |
| 70 | 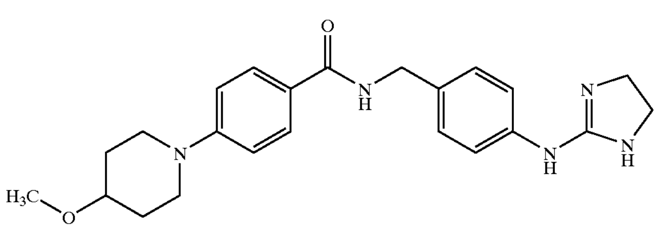 | N-[4-(4,5-Dihydro-1H-imidazol-2-ylamino)-benzyl]-4-(4-methoxy-piperidin-1-yl)-benzamide | 409 |
| 71 | 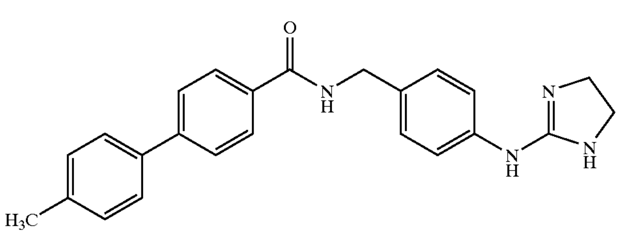 | 4'-Methyl-biphenyl-4-carboxylic acid 4-(4,5-dihydro-1H-imidazol-2-ylamino)-benzylamide | 385 |

TABLE 1-continued

| # | Name (Autonom ™) | M + H |
|---|---|---|
| 72 | 4'-Chloro-biphenyl-4-carboxylic acid 4-(4,5-dihydro-1H-imidazol-2-ylamino)-benzylamide | 406 |
| 73 | 4-(8-Aza-spiro[4.5]dec-8-yl)-N-[4-(4,5-di-hydro-1H-imidazol-2-ylamino)-benzyl]-benzamide | 433 |
| 74 | N-[4-(4,5-Dihydro-1H-imidazol-2-ylamino)-benzyl]-4-(1-ethyl-piperidin-4-yloxy)-benzamide | 423 |
| 75 | N-[4-(4,5-Dihydro-1H-imidazol-2-ylamino)-benzyl]-4-piperazin-1-yl-benzamide | 379 |
| 76 | N-[4-(4,5-Dihydro-1H-imidazol-2-ylamino)-benzyl]-4-(4-methyl-piperidin-1-yl)-benzamide | 393 |
| 77 | N-[4-(4,5-Dihydro-1H-imidazol-2-ylamino)-benzyl]-4-pyrimidin-2-yl-benzamide | 373 |
| 78 | 4-{4-[4-(4,5-Dihydro-1H-imidazol-2-ylamino)-benzyl-carbamoyl]-phenoxy}-piperidine-1-carboxylic acid ethyl ester | 467 |

TABLE 1-continued

| # | Name (Autonom ™) | M + H |
|---|---|---|
| 79 | N-{1-[4-(4,5-Dihydro-1H-imidazol-2-ylamino)-(S)-phenyl]-ethyl}-4-methoxy-benzamide | 339 |
| 80 | N-{1-[4-(4,5-Dihydro-1H-imidazol-2-ylamino)-(R)-phenyl]-ethyl}-4-methoxy-benzamide | 339 |
| 81 | N-[4-(4,5-Dihydro-1H-imidazol-2-ylamino)-benzyl]-4-(4-methyl-piperidine-1-sulfonyl)-benzamide | 457 |
| 82 | 4-tert-Butyl-N-[4-(4,5-dihydro-1H-imidazol-2-ylamino)-benzyl]-benzamide | 351 |
| 83 | N-[4-(4,5-Dihydro-1H-imidazol-2-ylamino)-benzyl]-4-pyrrolidin-1-yl-benzamide | 364 |
| 84 | N-[4-(4,5-Dihydro-1H-imidazol-2-ylamino)-benzyl]-4-(4-hydroxy-piperidin-1-yl)-benzamide | 394 |
| 85 | 4-(2-Chloro-thiophen-3-yl)-N-[4-(4,5-dihydro-1H-imidazol-2-ylamino)-benzyl]-benzamide | 412 |

TABLE 1-continued

| # | Structure | Name (Autonom ™) | M + H |
|---|---|---|---|
| 86 | 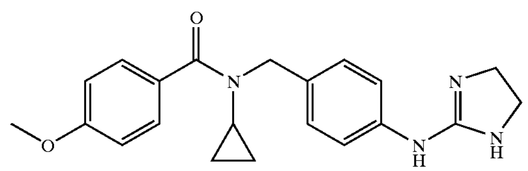 | N-Cyclopropyl-N-[4-(4,5-dihydro-1H-imidazol-2-ylamino)-benzyl]-4-methoxy-benzamide | 365 |
| 87 | 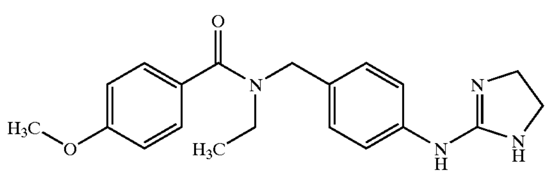 | N-[4-(4,5-Dihydro-1H-imidazol-2-ylamino)-benzyl]-N-ethyl-4-methoxy-benzamide | 353 |
| 88 | 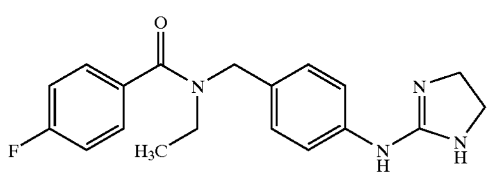 | N-[4-(4,5-Dihydro-1H-imidazol-2-ylamino)-benzyl]-N-ethyl-4-fluoro-benzamide | 341 |
| 89 | 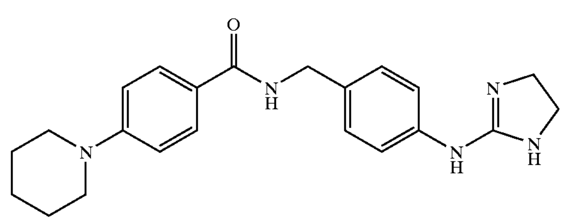 | N-[4-(4,5-Dihydro-1H-imidazol-2-ylamino)-benzyl]-4-piperidin-1-yl-benzamide | 378 |
| 90 | 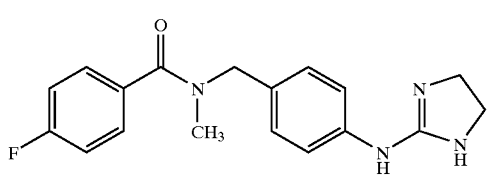 | N-[4-(4,5-Dihydro-1H-imidazol-2-ylamino)-benzyl]-4-fluoro-N-methyl-benzamide | 327 |
| 91 | 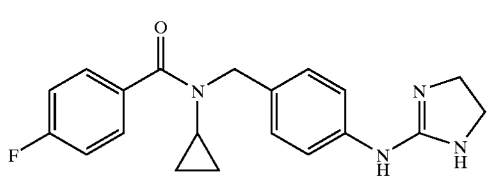 | N-Cyclopropyl-N-[4-(4,5-dihydro-1H-imidazol-2-ylamino)-benzyl]-4-fluoro-benzamide | 353 |
| 92 | 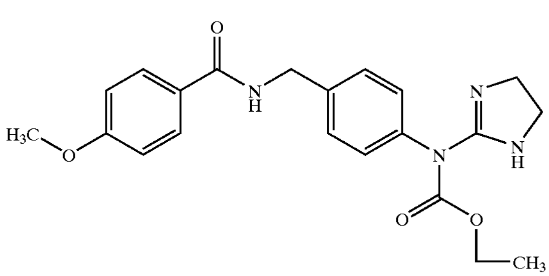 | (4,5-Dihydro-1H-imidazol-2-yl)-{4-[(4-methoxy-benzoylamino)-methyl]-phenyl}-carbamic acid ethyl ester | 397 |

TABLE 1-continued

| # | Structure | Name (Autonom ™) | M + H |
|---|---|---|---|
| 93 | 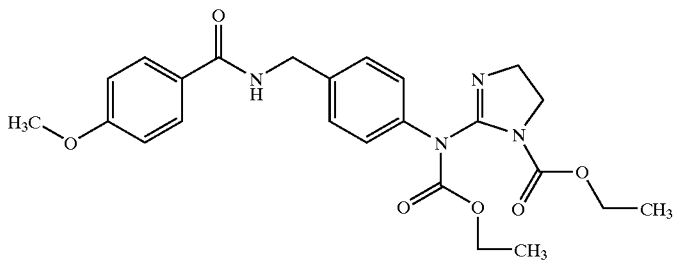 | 2-(Ethoxycarbonyl-{4-[(4-methoxy-benzoylamino)-methyl]-phenyl}-amino)-4,5-dihydro-imidazole-1-carboxylic acid ethyl ester | 470 |
| 94 | 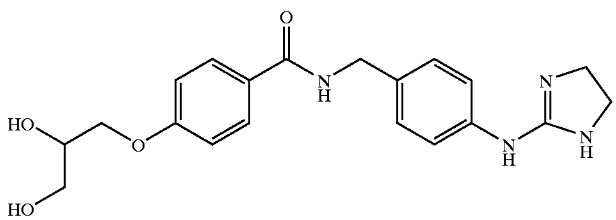 | N-[4-(4,5-Dihydro-1H-imidazol-2-ylamino)-benzyl]-4-(2,3-dihydroxy-propoxy)-benzamide | 385 |
| 95 | 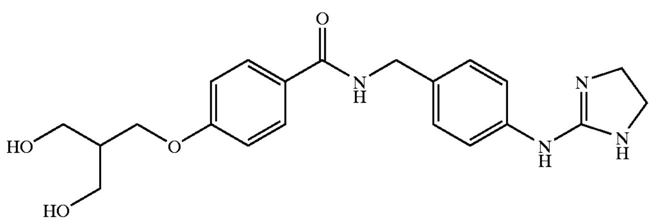 | N-[4-(4,5-Dihydro-1H-imidazol-2-ylamino)-benzyl]-4-(3-hydroxy-2-hydroxymethyl-propoxy)-benzamide | 399 |
| 96 | 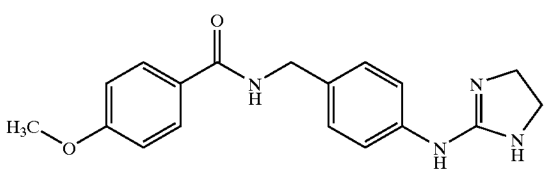 | N-[4-(4,5-Dihydro-1H-imidazol-2-yl-amino)-benzyl]-4-methoxy-benzamide | |
| 97 | 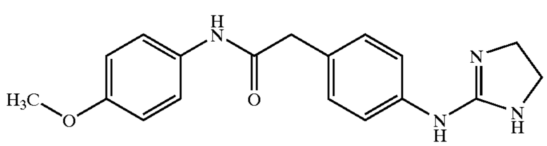 | 2-[4-(4,5-Dihydro-1H-imidazol-2-yl-amino)-phenyl]-N-(4-methoxy-phenyl)-acetamide. | |
| 98 | 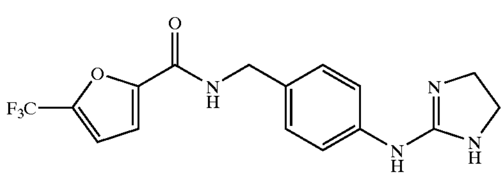 | 5-Trifluoromethyl-furan-2-carboxylic acid 4-(4,5-dihydro-1H-imidazol-2-ylamino)-benzylamide | 299 |
| 99 | 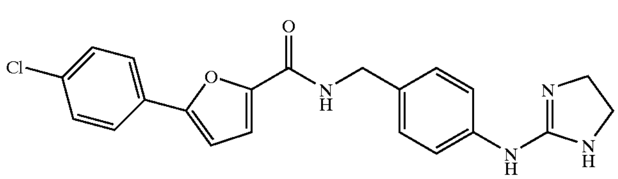 | 5-(4-Chloro-phenyl)-furan-2-carboxylic acid 4-(4,5-dihydro-1H-imidazol-2-ylamino)-benzylamide | 396 |

General Synthetic Scheme

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–20; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Schemes A and B describe alternative methods to generate the compounds of the invention. Scheme A illustrates a preferred procedure for preparation of compounds of the embodiment of formula II, wherein X is halo or other leaving group, and n, p, $R^2$, $R^a$, $R^b$ and $R^c$ are as described herein. The procedure of Scheme A is exemplary, and alternative synthetic routes to the compounds of the invention will suggest themselves to those skilled in the art.

SCHEME A

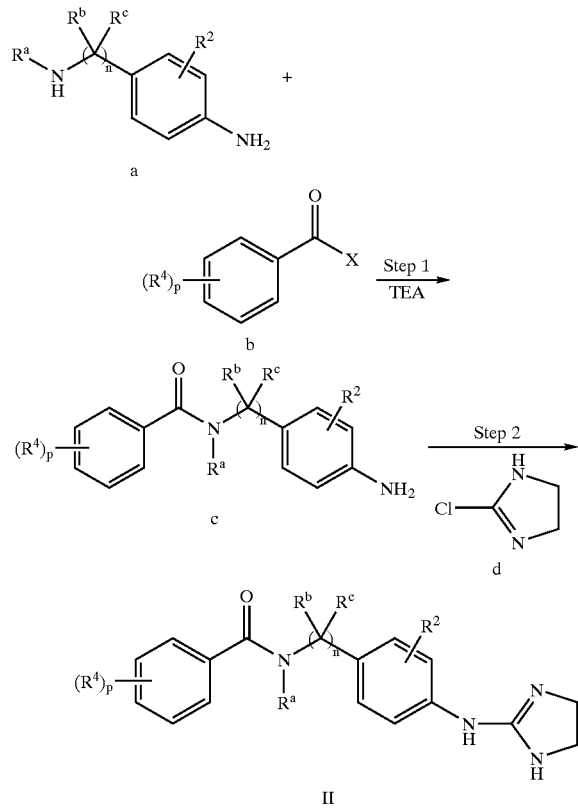

In step 1 of Scheme A, an aminoalkyl arylamine a is reacted with an aroyl halide b, to afford an aryl amide compound c. Step 1 is a straightforward condensation reaction that provides quantitative or substantially quantitative yields under mild conditions using a variety of aminoalkyl arylamine such as 4-aminomethyl-phenylamine with various aroyl halides. The aroyl halide b is shown as an optionally substituted benzoyl halide. Numerous substituted benzoic acid compounds are commercially available, and the acid chloride compounds of such compounds may be used in this step. The aroyl halide b may alternatively comprise other types of aroyl halide, including naphthalene carbonyl halides such as naphthalene-1-carbonyl halide and naphthalene-2-carbonyl halide, which may optionally be substituted. In other embodiments of the invention aroyl halide b may be replaced with various heteroaroyl halides such as quinoline-5-carbonyl halide, quinoline-6-carbonyl halide, isoquinoline-5-carbonyl halide, isoquinoline-6-carbonyl halide, isonicotinoyl halide, pyrimidine-4-carbonyl halide, furan-3-carbonyl halide, thiophen-3-carbonyl halide, and the like, which again may optionally be substituted. Also usable in place of aroyl halide b are substituted benzoic anhydrides and heteroaromatic carboxylic anhydrides.

The aryl amide compound c of step 1 may then, in step 2, be heated with 2-chloroimidazoline sulfate under polar protic solvent conditions to provide an imidazolinylamino-substituted arylamide of formula II.

Many variations on the procedure of Scheme A are possible. Where substituents $R^2$ and/or $R^4$ are incompatible with or otherwise sensitive to the chemistry of step 1 or step 2, suitable protecting group strategies may be utilized. Numerous well-known protecting group schemes may be used in this regard. Exemplary protecting group strategies are described by, for example, Greene et al. in *Protecting Groups in Organic Synthesis,* 3rd. Ed., Wiley & Sons, 1999. In certain embodiments, although generally less preferred, chloroimidazoline may first be reacted with aminoalkyl aniline a, provided that the suitable protection of amino groups is made to prevent unwanted reaction. The resulting product can then be deprotected or partially deprotected and reacted with aroyl halide b to yield imidazolinylamino-substituted arylamide II.

Scheme B illustrates a preferred procedure for preparation of compounds of the embodiment of formula III, wherein n, p, $R^2$, $R^a$, $R^b$ and $R^c$ are as described herein.

SCHEME B

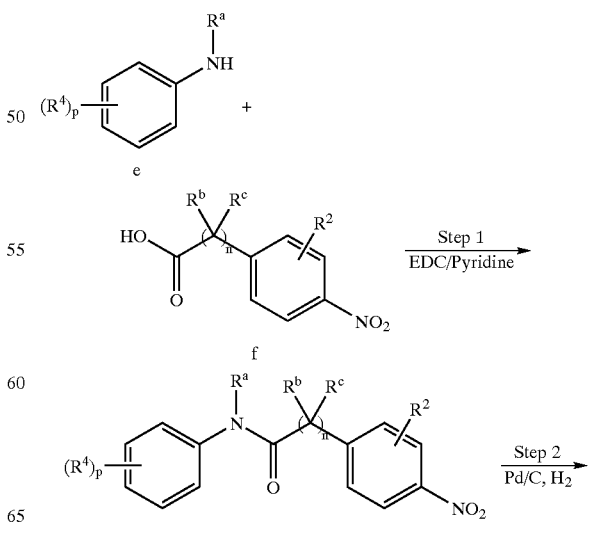

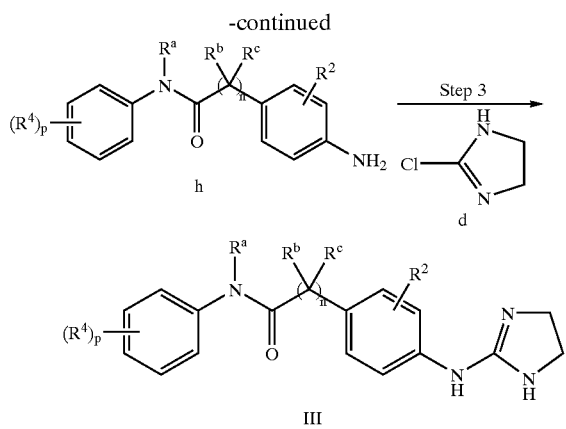

III

In step 1 of Scheme B, an aryl amine e is reacted with a nitroarylalkyl carboxylic acid f in the presence of a carbodiimide such as EDC (1-(3-dimethylaminopropyl)-3-ethylcarbodiimide hydrochloride) to yield a nitro-substituted aryl amide compound g. The aryl amine e used in this step may comprise an optionally substituted phenylamine, many of which are commercially available, or an optionally substituted naphthalenylamine such as naphthalen-1-ylamine or naphthalen-2-ylamine. Alternatively, the compound e may comprise an optionally substituted heteroaryl amine such as pyridin-4-ylamine, pyrimidin-5-ylamine, quinolin-5-ylamine, quinolin-6-ylamine, isoquinolin-5-ylamine, isoquinolin-6-ylamine, thiophen-3-ylamine, furan-3-ylamine, or the like.

The nitro-substituted aryl amide g of step 1 is reduced in step 2 to provide an aminoarylalkyl carboxylic acid h. The reduction of step 2 may be carried out using a platinum or palladium catalyst on activated carbon in the presence of hydrogen under mild conditions.

The aminoarylalkyl carboxylic acid compound h of step 2 may then, in step 3, be heated with 2-chloroimidazoline sulfate under polar protic solvent conditions to provide an imidazolinylamino-substituted aryl amide of formula III.

The procedure of Scheme B, like that of Scheme A, is only exemplary and many alternate procedures and variations will be apparent to those skilled in the art. For example, the nitro-substituted aryl amide compound g of step 1 may be replaced by an aminoarylalkyl carboxylic acid compound wherein the amino group is protected. In this case, step 2 would involve deprotection to provide the free amino group instead of reduction of a nitro group. In another variation of the procedure of Scheme B, an amino-substituted aryl amide compound could first be reacted with chloroimidazoline, and the resulting product, using a suitable protection strategy, may then be reacted with aryl amine e to provide the aryl amide III.

General Utility

The compounds of the present invention are IP receptor modulators, in particular, IP receptor antagonists, and as such possess selective antagonist activity at the IP receptor. These compounds (and compositions containing them) are expected to be useful in the prevention and treatment of a variety of diseases in mammals, especially humans. The compounds of the invention also exhibit little or no hERG channel inhibition and thus are not expected to cause unwanted cardiovascular side effects.

In particular, the compounds of the invention possess anti-inflammatory and/or analgesic properties in vivo, and accordingly, are expected to find utility in the treatment of disease states associated with pain conditions from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The compounds of the present invention are also useful in the treatment of inflammatory conditions from a variety of causes, including, but not limited to, bacterial, fungal or viral infections, rheumatoid arthritis, osteoarthritis, surgery, bladder infection or idiopathic bladder inflammation, overuse, old age, or nutritional deficiencies, prostatitis, and conjunctivitis.

The compounds of this invention are also useful in treating disease states associated with urinary tract disease states associated with bladder outlet obstruction and urinary incontinence conditions such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urge incontinence, urethritis, prostatitits, pelvic pain syndrome, prostatodynia, cystitis, and idiophatic bladder hypersensitivity, and other symptoms related to overactive bladder.

The compounds of this invention may also find utility in the treatment of hypotensive vascular diseases such as hypotension associated with septic shock.

In addition, the compounds of this invention are useful in the treatment of respiratory diseases such as allergies and asthma.

These and other therapeutic uses are described, for example, in Goodman & Gilman's, The Pharmacological Basis of Therapeutics, tenth edition, McGraw-Hill, New York, 2001, Chapter 26; and Coleman, R. A., Pharmacological Reviews, 1994, 46:205–229.

Testing

The anti-inflammatory/analgesic activity of the compounds of this invention may be assayed by in vivo assays such as the Rat Carrageenan-Induced Mechanical Hyperalgesia Paw Assay and the Rat Complete Freund's Adjuvant-Induced Mechanical Hyperalgesia Assay, as described in more detail in the following Examples. Activity in the inhibition of bladder contractions may be assayed by in vivo assays such as the Inhibition of Bladder Contractions Induced by Isovolumetric Bladder Distension Assay and the Inhibition of Volume-Induced Contracts in Rats Assay, as described in more detail in the Examples below. Activity in the inhibition of the septic shock may be assayed by in vivo assays such as the Rat Reversal of Endotoxin-Induced Hypotension Assay, as described in more detail in the Examples below. The level of hERG channel inhibition of the compounds of the invention were assayed according to the procedure described in the Examples.

Administration and Pharmaceutical Composition

The present invention includes pharmaceutical compositions comprising at least one compound of the present invention, or individual isomers, racemic or non-racemic mixtures of isomers, or pharmaceutically acceptable salts or solvates thereof, together with at least one pharmaceutically acceptable carrier and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration.

The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 11 to 17.

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

EXAMPLES

The following preparations and examples are given to enable those skilled in the art to more clearly understand and to practice the present invention. They should not be considered as limiting the scope of the invention, but merely as being illustrative and representative thereof.

Example 1

N-[4-(Imidazolidin-2-ylideneamino)-benzyl]-4-methoxy-benzamide

The synthetic procedures used in this Example are outlined in Scheme C.

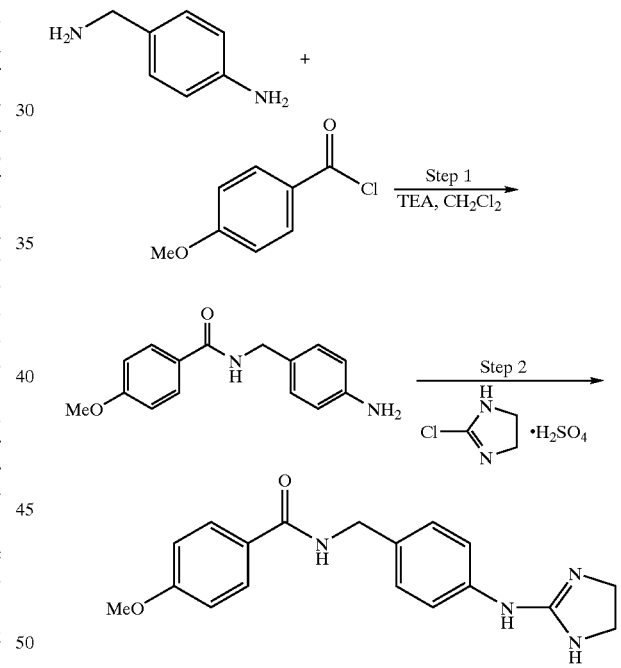

Step 1

N-(4-Aminobenzyl)-4-methoxybenzamide

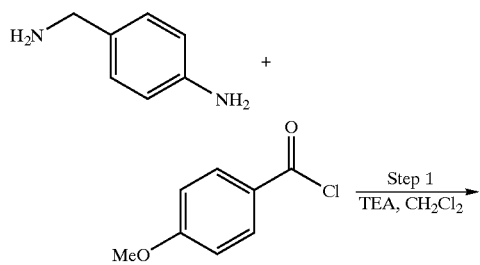

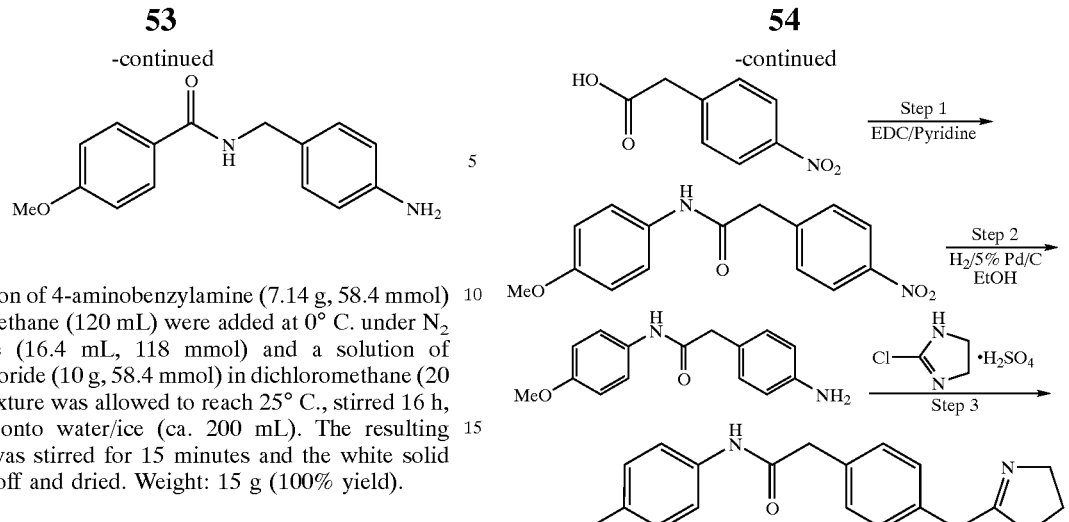

To a solution of 4-aminobenzylamine (7.14 g, 58.4 mmol) in dichloromethane (120 mL) were added at 0° C. under $N_2$ triethylamine (16.4 mL, 118 mmol) and a solution of p-anisoyl chloride (10 g, 58.4 mmol) in dichloromethane (20 mL). The mixture was allowed to reach 25° C., stirred 16 h, and poured onto water/ice (ca. 200 mL). The resulting suspension was stirred for 15 minutes and the white solid was filtered off and dried. Weight: 15 g (100% yield).

Step 2

N-[4-(4,5-Dihydro-1H-imidazol-2-ylamino)-benzyl]-4-methoxybenzamide

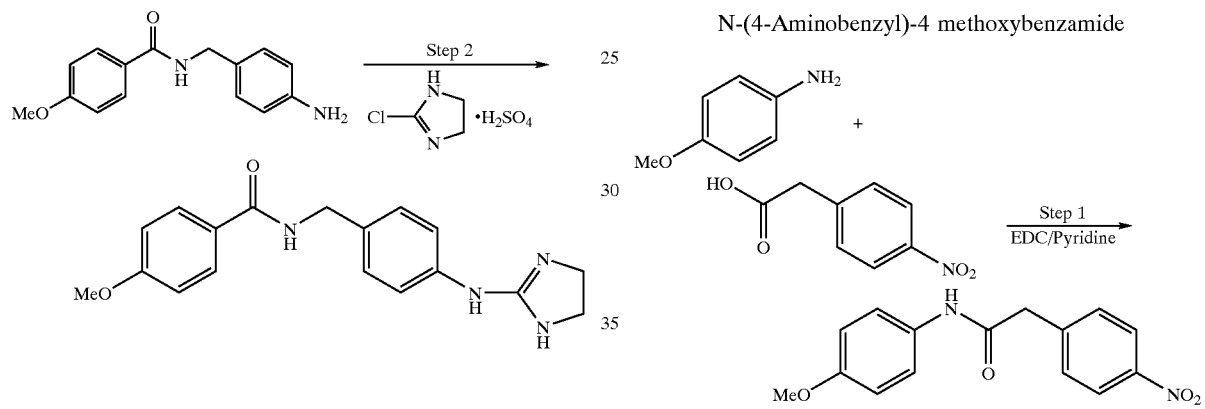

A mixture of N-(4-Aminobenzyl)-4-methoxybenzamide (15 g, 58.4 mmol), 2-chloroimidazoline sulfate (15.2 g, 74 mmol) and 2-propanol (380 mL) was heated at reflux for 2.5 h under $N_2$. The mixture was cooled to 0° C. and filtered, and the filtrate was concentrated to dryness. To the resulting residue 10% aqueous sodium hydroxide was added to reach pH 13–14. The resulting suspension was filtered, and the solid N-[4-(4,5-dihydro-1H-imidazol-2-ylamino)-benzyl]-4-methoxybenzamide was crystallized from dichloromethane. Weight 11.9 g (61.4% yield). mp 160.3–160.6° C.

Additional compounds made by the above procedure are shown in Table 1.

Example 2

2-[4-(Imidazolidin-2-ylideneamino)-phenyl]-N-(4-methoxy-phenyl)-acetamide

The synthetic procedures used in this Example are outlined in Scheme D

SCHEME D

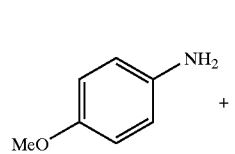

+

Step 1

N-(4-Aminobenzyl)-4 methoxybenzamide

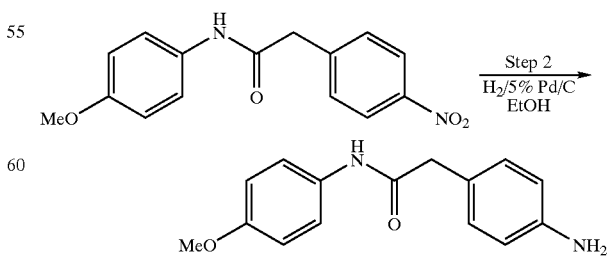

A mixture of p-anisidine (4.92 g, 40 mmol), 4-nitrophenylacetic acid (7.25 g, 40 mmol) and 1-(3-dimethylaminopropyl)-3-ethylcarbodiimide hydrochloride (EDC) (11.5 g, 60 mmol) in pyridine (40 mL) was stirred at room temperature overnight. The solvent was evaporated, and HCl (1M, 50 mL) was added. The resulting product was filtered and washed with water and ether, and recrystallized from ethanol to give N-(4-Methoxyphenyl)-2-(4-nitrophenyl)-acetamide (9.6 g, 84%).

Step 2

2-(4-Amino-phenyl)-N-(4-methoxy-phenyl)-acetamide

A mixture of N-(4-Methoxy-phenyl)-2-(4-nitro-phenyl)-acetamide (859 mg, 3 mmol), 5% Pd on C (16 mg) and EtOH (20 mL) was stirred under a hydrogen atmosphere (1 atm) for 5 hr. Filtration of the catalyst and evaporation of the solvent afforded 2-(4-Amino-phenyl)-N-(4-methoxy-phenyl)-acetamide (732 mg, 95%).

Step 3

2-[4-(Imidazolidin-2-ylideneamino)-phenyl]-N-(4-methoxy-phenyl)-acetamide hydrochloride

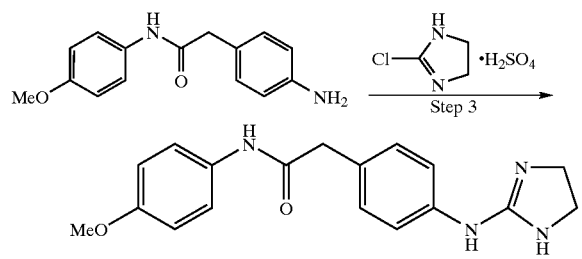

2-(4-Amino-phenyl)-N-(4-methoxy-phenyl)-acetamide (732 mg) was treated with 2-chloroimidazoline sulfate using the procedure of Example 1 above, to yield 2-[4-(Imidazolidin-2-ylideneamino)-phenyl]-N-(4-methoxy-phenyl)-acetamide hydrochloride (10%); Mass Spec M+H: 314.

Example 3

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 4
IP Receptor Agonist Activity Assay

The IP receptor agonist potency of compounds of this invention in vitro was determined by measuring the agonist-mediated cyclic AMP accumulation in an assay utilizing Chinese Hamster Ovary cells expressing the rat prostanoid IP receptor. Cyclic AMP levels were determined using a commercially available Adenylate Cyclase cAMP Flashplate Assay.

Chinese Hamster Ovary cells expressing the rat prostanoid IP receptor were maintained in Ham's Mixture with 10% fetal bovine serum, 250 µg/ml geneticin in 5% carbon dioxide (95% $O_2$). Cells were harvested at approximately 90% confluency using Dulbecco's Phosphate-Buffered saline containing 2 mM EDTA, and washed once at 1000×g and resuspended in Wash Buffer. A sample was aliquoted for protein determination. The cell suspension was centrifuged at 1000×g and adjusted to 110–140 E+3 cells/50 µl in the "Stimulation and Detection Buffer" from the assay kit.

The test compounds or vehicle were incubated with 50 µl cells (110–140 E+3 cells) for 5 minutes at room temperature. After the incubation, 100 µl lysis/tracer solution was added to the wells and the radioactivity counted on a Packard Topcount microplate scintillation counter after overnight incubation. The amount of radioactive cAMP bound to the antibody is inversely proportional to the concentration of added non-radioactive cAMP. The $pEC_{50}$ values were then determined and compared against standard agonists values.

The compounds of the invention were active in this assay. The compound N-[4-(4,5-Dihydro-1H-imidazol-2-yl-amino)-benzyl]-4-methoxy-benzamide, for example, showed a pKi of approximately 8.12.

Example 5
Carrageenan-Induced Mechanical Hyperalgesia Assay

The anti-inflammatory/analgesic activity of compounds of this invention was determined by the Carrageenan-Induced Mechanical Hyperalgesia Assay by measuring the inhibition of carrageenan-induced paw hyperalgesia in the rat, using a modification of the method described in L. O. Randall and J. J. Selitto, *Archives of International Pharmacodynamics*, 1957, 11, 409–419, and Vinegar et al., *Journal of Pharmacology and Experimental Therapeutics*, 1969, 166, 96–103.

Male Sprague-Dawley rats (130–150 g) were weighed and randomly assigned to treatment groups (n=10). To induce mechanical hyperalgesia, rats were lightly anesthetized with halothane and administered 1% carrageenan or vehicle 1 (100 µl) in the plantar surface of the left hindpaw. Rats were administered vehicle (10 ml/kg, p.o. or 1 ml/kg, i.v) or compounds of this invention (at 1, 3, 10, 30 and 100 mg/kg, p.o.) or (0.3, 1.0, 3.0 and 10 mg/kg, i.v.) one hour before testing. Mechanical hyperalgesia was measured using an Analgesy-meter (UGO BASILE, Biological Research Apparatus, Comerio, Italy). The vehicle- or carrageenan-treated hindpaw was placed on the dome of the apparatus, plantar surface facing down. A constantly increasing force was then applied to the dorsal surface of the paw. The force at which the rat withdrew its paw, struggled, or vocalized was considered the end point.

Treatment groups were compared using a one-way analysis of variance on the paw withdrawal force (RESP). Pairwise comparisons for the drug-treated groups to the vehicle group were made using Fisher's LSD strategy and Dunn's procedure. Percent inhibition of mechanical hyperalgesia was calculated for each animal, and the average $ID_{50}$ value was estimated using the following sigmoidal model:

$$\% \text{ inhibition} = 100/(1+\exp((ID_{50}-\text{dose})/N))$$

where $ID_{50}$ is the dose of the compound needed to inhibit half of the maximum response (i.e., 100% in this model) and N is a curvature parameter. The compounds of this invention were active in this assay.

Example 6
Complete Freund's Adjuvant-Induced Mechanical Hyperalgesia Assay

The anti-inflammatory/analgesic activity of compounds of this invention may also be determined using an adjuvant-induced arthritis pain model in the rat, where pain is assessed by the animal's response to the squeezing of the inflamed foot, using a modification of the method described in J. Hylden et al., *Pain* 1989, 37, 229–243. The modification includes the assessment of hyperalgesia instead of changes in activity of spinal cord neurons.

Briefly, rats were weighed and randomly assigned to treatment groups. To induce mechanical hyperalgesia, rats were lightly anesthetized with halothane and 100 µl of Complete Freund's Adjuvant or saline was administered into the plantar surface of the left hindpaw. Twenty-four hours later, water (vehicle) or compounds of this invention were orally administered to the rats one hour before testing. Mechanical hyperalgesia was measured using an Analgesy-meter (UGO BASILE, Biological Research Apparatus, Comerio, Italy). The saline or carrageenan-treated hindpaw was placed on the dome of the apparatus, plantar surface facing down. A constantly increasing force was then applied to the dorsal surface of the paw, and the force at which the rat withdrew its paw, struggled, or vocalized was considered the end point. The treatment groups were compared using a one-way analysis of variance on the paw withdrawal force. Percent inhibition was calculated for each animal in the form:

$$100 \times ((c/d-c/v) \div (s/v-c/v))$$

where c/d is the paw withdrawal force for the carrageenan-treated paw in an animal to which drug has been administered; c/v is the paw withdrawal force for the carrageenan-treated paw in an animal to which vehicle has been administered; and s/v is the paw withdrawal force for the saline-treated paw in an animal to which vehicle has been administered. Significance was determined using Student's t-test. The compounds of the invention were active in this assay.

Example 7
Inhibition of Bladder Contractions Induced by Isovolumetric Bladder Distension in Rats The inhibition of bladder contractions was determined by an assay using a modification of the method described in C. A. Maggi et al., *J. Pharm. and Exper. Therapeutics*, 1984, 230, 500–513.

Briefly, male Sprague-Dawley rats (200–250 g) were weighed and randomly assigned to treatment groups. A catheter was inserted through the urethra into the bladder to induce bladder contractions, and a warm saline solution (5 mL) was infused. Rhythmic contractions were produced in about 30% of the animals. The compounds of the invention (0.1, 0.3 or 1 mg/kg) were administered intravenous at the onset of regular rhythmic contractions. The effects on rhythmic contracts were then measured. The compounds of this invention were active in this assay.

Example 8
Inhibition of Volume-Induced Contractions in Rats

The inhibition of bladder contractions was determined by an assay using a modification of the method described in S. S. Hegde et al., *Proceedings of the 26th Annual Meeting of the International Continence Society* (Aug. 27th–30th) 1996, Abstract 126.

Female Sprague-Dawley rats were anesthetized with urethane and instrumented for intravenous administration of drugs and, in some cases, measurement of arterial-pressure, heart rate and intra-bladder pressure. The effect of test compounds on volume-induced bladder contractions was determined in separate groups of animals. Volume-induced reflex bladder contractions were induced by filling the bladder with saline.

The test compounds were administered intravenously in a cumulative manner at 10-minute intervals. Atropine (0.3 mg/kg, iv) was administered at the end of the study as a positive control. The compounds of this invention were active in this assay.

Example 9
Reversal of Endotoxin-Induced Hypotension in Rats

Septic shock, sometimes referred to as endotoxic shock, is caused by the presence of infectious agents, particularly bacterial endotoxins, in the bloodstream and is characterized by hypotension and organ dysfunction. Many symptoms of septic shock, in particular, hypotension, are induced in the rat by the administration of bacterial endotoxins. The ability of a compound to inhibit endotoxin-induced hypotension is therefore predictive of the utility of the compound in the treatment of septic or endotoxic shock.

The activity of the compounds of the invention in the treatment of septic or endotoxic shock was determined by measuring the reversal of endotoxin-induced hypotension in the rat, using a modification of the method described in M. Giral et al., *British Journal of Pharmacology*, 1969, 118, 1223–1231.

Briefly, adult rats (>200 g) were anesthetized with an inhalation anesthetic and femoral arteries and veins were cannulated for insertion of blood pressure transducers and drug administration lines, respectively. They were placed in Mayo restrainers while still under the influence of the anesthetic. After recovery from anesthesia and stabilization of heart rate and blood pressure (which typically required about 30 minutes), endotoxin (50 mg/kg *E. coli* and 25 mg/kg *Salmonella*) was administered intravenously. Changes in blood pressure and heart rate were monitored. After one hour, compounds of this invention or vehicle were also administered intravenously, and cardiovascular parameters were continuously monitored for the next three hours. Responses are represented as percentage return to initial diastolic blood pressure. Significance was determined using Student's t-test. The compounds of this invention were active in this assay.

Example 10
hERG Potassium Channel Pharmacology Screening

The effects of the subject compounds on recombinant hERG potassium channels expressed in CHO-K1 cells was determined according to the procedure reported by Hamill et al., 1981, *Pflügers Arch.*, 391, 85–100

The following solutions were used to isolate potassium currents in cultured cell lines: extracellular (in mM), NaCl (150), KCl (4), HEPES (10), $CaCl_2$ (1.2), $MgCl_2$ (1), adjusted to pH 7.4 with NaOH; intracellular (in mM), KCl (140), HEPES (10), EGTA (5), $MgCl_2$ (6), ATP-$Na_2$ (5), adjusted to pH 7.2 with KOH.

Whole-cell patch-clamp methods were used to record potassium currents from CHO.K1 cells expressing the human hERG channel. Each cell was held at a negative holding potential of −80 mV. At the beginning of each experiment, currents were characterized by obtaining current-voltage relationships. Cells were depolarized from −80 mV to +40 mV for 1 second followed by a 300 ms repolarization to potentials between −120 and +20 mV (in 20 mV increments). The stimulation frequency is 0.1 Hz. Peak tail current amplitudes at the different test potentials were measured to obtain the current-voltage relationship.

A second protocol was used to investigate the effects of compounds on hERG currents. Cells were depolarized from −80 mV to +20 mV for 500 ms and then repolarized to −40 mV for 500 ms, followed by a 200 ms hyperpolarizing pulse to −120 mV. At the end of the hyperpolarizing pulse, the cells were returned to a holding potential of −80 mV. Data points were collected at a frequency of 0.1 Hz (1 stimulus every 10 seconds) using pClamp 8.0 software from Axon Instruments in Clampex mode. Drugs were applied once a stable baseline has been recorded for 5 min. Data are collected for 5 or 10 minute blocks. The number of stimuli and therefore blocks of data for a given drug concentration depends on how quickly the drug reaches equilibrium.

If a compound had an effect on current amplitude, the reversibility of the effect was examined by returning the buffer to control solution. Compounds affecting the current were washed out and higher concentrations of the compound was applied to the same cells following full recovery.

Voltage-dependent potassium currents were recorded from single cells at room temperature (20–22° C.) using the whole-cell configuration of the patch-clamp technique. Cells were voltage-clamped using a patch-clamp amplifier (e.g., Axopatch 200; Axon Instruments) which is controlled by computer via a Digidata 1200 Interface (Axon Instruments). The voltage-clamp protocols used in this Example were generated using PClamp software (version 7 or later; Axon Instruments). Whole-cell currents were low-pass filtered (1–2 kHz, 4-pole Bessel), digitized (10 kHz) and stored on magnetic medium for off-line analysis using PClamp software, Microcal Origin, and Prism.

The peak amplitude of outward currents are measured using Clampfit software to find peak amplitude. The peak amplitudes of the inward tail currents evoked are fit using a single exponential function:

$$f(t) = \sum_{i=1}^{n} A_i e^{(-t/\tau_i)} + C$$

where A indicates the peak current, C is the plateau or anti-peak, and T is the time constant. The Chebyshev search method with a four point smoothing function was applied.

Once the tail currents were fit and peak amplitudes measured, the effects of the compound were determined as a % change compared to the peak amplitudes of the control peaks.

Statistics were calculated using Microcal Origin and Prism software, and results were reported as mean +/− standard error of the mean. A minimum of 3 cells/concentration of compound was required for testing of each compound.

A compound, cisapride, known to inhibit hERG potassium channels, was used as a standard compound and a full concentration-response curve for cisapride was generated for comparison with the subject compounds.

The compounds of the invention did not significantly inhibit the hERG potassium channel using the above assay. Notably, the hERG outward current inhibition percentage for the representative compound N-[4-(4,5-Dihydro-1H-imidazol-2-yl-amino)-benzyl]-4-methoxy-benzamide was 4.3±4.4% at 1 uM, and 10.8±7.2% at 10 uM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

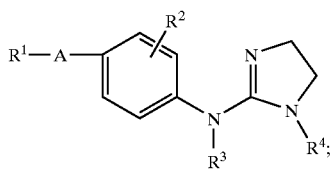

wherein:
$R^1$ is optionally substituted aryl;
$R^2$ is hydrogen, alkyl, alkoxy, haloalkyl or halogen;
$R^3$ and $R^4$ each independently is hydrogen or alkoxycarbonyl;
A is —C(O)—NR$^a$—(CR$^b$R$^c$)$_n$— or —NR$^a$—C(O)—(CR$^b$R$^c$)$_n$—;
n is from 1 to 6;
$R^a$ is hydrogen, alkyl or cycloalkyl; and
$R^b$ and $R^c$ each independently is hydrogen or alkyl;
or a pharmaceutically acceptable salt, or solvate thereof.

2. The compound of claim 1, wherein A is —C(O)—NR$^a$—(CR$^b$R$^c$)$_n$—.

3. The compound of claim 2, wherein n is 1.

4. The compound of claim 3, wherein $R^3$, $R^4$, $R^a$, $R^b$ and $R^c$ are hydrogen.

5. The compound of claim 4, wherein $R^1$ is optionally substituted phenyl.

6. The compound of claim 5, wherein $R^1$ is phenyl optionally substituted by one, two, or three substituents independently selected from alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino.

7. The compound of claim 5, wherein $R^1$ is phenyl optionally substituted with alkyl, alkoxy, alkenyl, optionally substituted phenyl, optionally substituted heteroaryl, optionally substituted heterocyclyl, haloalkyl, alkoxy, nitro, cyano, or halogen.

8. The compound of claim 5, wherein $R^1$ is 4-alkoxyphenyl.

9. The compound of claim 5, wherein $R^1$ is 4-alkylphenyl.

10. The compound of claim 5, wherein $R^1$ is 4-phenoxyphenyl wherein the phenoxy moiety is optionally substituted.

11. The compound of claim 5, wherein $R^1$ is 4-cycloalkyloxyphenyl.

12. The compound of claim 5, wherein $R^1$ is 4-cycloalkylalkoxyphenyl.

13. The compound of claim 5, wherein $R^1$ is 4-alkoxyalkyloxyphenyl.

14. The compound of claim 5, wherein $R^1$ is 4-hydroxyalkyloxyphenyl.

15. The compound of claim 5, wherein $R^1$ is 4-dialkylaminophenyl.

16. The compound of claim 5, wherein $R^1$ is 4-halophenyl.

17. The compound of claim 5, wherein $R^1$ is optionally substituted 4-biphenyl.

18. The compound of claim 5, wherein $R^1$ is 4-cyanophenyl.

19. The compound of claim 5, wherein $R^1$ is 4-alkenylphenyl.

20. The compound of claim 5, wherein $R^1$ is 4-cycloalkylphenyl.

21. The compound of claim 5, wherein $R^1$ is 4-benzyloxyphenyl.

22. The compound of claim 5, wherein $R^1$ is 4-dialkylsulfamoylphenyl.

23. The compound of claim 5, wherein $R^1$ is 4-alkylsulfamoylphenyl.

24. The compound of claim 5, wherein $R^1$ is 4-heteroarylphenyl wherein the heteroaryl moiety is optionally substituted.

25. The compound of claim 5, wherein $R^1$ is 4-heterocyclyphenyl wherein the heterocyclyl moiety is optionally substituted.

26. The compound of claim 5, wherein $R^1$ is 4-heterocycyloxyphenyl wherein the heterocyclyl moiety is optionally substituted.

27. The compound of claim 5, wherein $R^1$ is 4-heterocycylalkyloxyphenyl wherein the heterocyclyl moiety is optionally substituted.

28. The compound of claim 5, wherein $R^1$ is 4-heterocycylsulfonylphenyl wherein the heterocyclyl moiety is optionally substituted.

29. The compound of claim 1, wherein A is —NR$^a$—C(O)—(CR$^b$R$^c$)$_n$—.

30. The compound of claim 29, wherein n is 1.

31. The compound of claim 30, wherein $R^a$ is hydrogen, alkyl or cycloalkyl, and $R^b$ and $R^c$ each independently is hydrogen or alkyl.

32. The compound of claim 31, wherein $R^1$ is phenyl optionally substituted by one, two, or three substituents independently selected from alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino.

33. The compound of claim 1, wherein said compound is of the formula II:

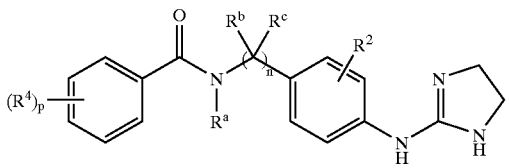

II wherein:
p is from 0 to 4;
$R^4$ is alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino;
$R^a$ is hydrogen, alkyl or cycloalkyl;
$R^b$ and $R^c$ each independently is hydrogen or alkyl; and
n and $R^2$ are as defined in claim 1.

34. The compound of claim 33, wherein $R^b$ and $R^c$ are hydrogen.

35. The compound of claim 34, wherein n is 1.

36. The compound of claim 16, wherein p is 1.

37. The compound of claim 1, wherein said compound is of the formula III:

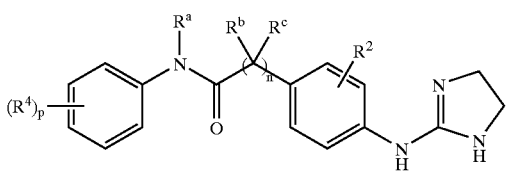

III wherein:
p is from 0 to 4;
$R^4$ is alkyl, alkenyl, alkoxy, optionally substituted aryl, optionally substituted aryloxy, aralkyloxy, halogen, haloalkyl, haloalkoxy, hydroxy, hydroxyalkyl, alkylsulfonyl, alkoxyalkyloxy, hydroxyalkyloxy, nitro, cyano, hydroxy, cycloalkyl, cycloalkyloxy, cycloalkylalkoxy, amino, alkylamino, dialkylamino, methylenedioxy, ethylenedioxy, optionally substituted heterocyclyl, optionally substituted heterocyclyloxy, optionally substituted heterocyclylsulfonyl, optionally substituted heterocyclylalkyloxy, optionally substituted heteroaryl, sulfamoyl, alkylsulfamoyl, dialkylsulfamoyl or sulfonylamino;
$R^a$ is hydrogen, alkyl or cycloalkyl;
$R^b$ and $R^c$ each independently is hydrogen or alkyl; and
n and $R^2$ are as defined in claim 1.

38. The compound of claim 33, wherein said compound is of the formula IV:

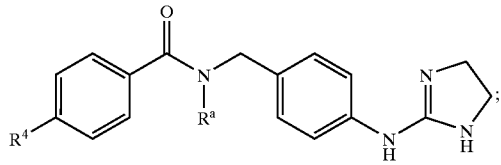

IV and wherein $R^4$ and $R^a$ are as defined in claim 32.

39. The compound of claim 38, wherein $R^4$ is alkoxy selected from methoxy, ethoxy, propoxy, isopropoxy, butoxy or isobutoxy.

40. The compound of claim 38, wherein $R^4$ is alkyl selected from methyl, ethyl, propyl, isopropyl, butyl or isobutyl.

41. The compound of claim 38, wherein $R^4$ is aryloxy.

42. The compound of claim 38, wherein $R^4$ is cycloalkyloxy.

43. The compound of claim 38, wherein $R^4$ is cycloalkylalkoxy.

44. The compound of claim 38, wherein $R^4$ is alkoxyalkyloxy.

45. The compound of claim 38, wherein $R^4$ is hydroxyalkyloxy.

46. The compound of claim 38, wherein $R^4$ is dialkylamino.

47. The compound of claim 38, wherein $R^4$ is halo selected from fluoro, chloro or bromo.

48. The compound of claim 38, wherein $R^4$ is optionally substituted phenyl.

49. The compound of claim 38, wherein $R^4$ is cyano.

50. The compound of claim 38, wherein $R^4$ is alkenyl.

51. The compound of claim 38, wherein $R^4$ is cycloalkyl.

52. The compound of claim 38, wherein $R^4$ is optionally substituted aryloxy.

53. The compound of claim 38, wherein $R^4$ is dialkylsulfamoyl.

54. The compound of claim 38, wherein $R^4$ is alkylsulfamoyl.

55. The compound of claim 38, wherein $R^4$ is heteroaryl wherein the heteroaryl moiety is optionally substituted.

56. The compound of claim 38, wherein $R^4$ is heterocyclyl wherein the heterocyclyl moiety is optionally substituted.

57. The compound of claim 38, wherein $R^4$ is heterocycloxy wherein the heterocyclyl moiety is optionally substituted.

58. The compound of claim 38, wherein $R^4$ is heterocyclalkyloxy wherein the heterocyclyl moiety is optionally substituted.

59. The compound of claim 38, wherein $R^4$ is heterocylsulfonyl wherein the heterocyclyl moiety is optionally substituted.

60. The compound of claim 1, selected from:
N-[4-(4,5-Dihydro-1H-imidazol-2-yl-amino)-benzyl]-4-methoxy-benzamide;
(4,5-Dihydro-1H-imidazol-2-yl)-{4-[(4-methoxy-benzoylamino)-methyl]-phenyl}-carbamic acid ethyl ester;

N-[4-(4,5-Dihydro-1H-imidazol-2-ylamino)-benzyl]-2,4-difluoro-benzamide;
N-[4-(4,5-Dihydro-1H-imidazol-2-ylamino)-benzyl]-4-fluoro-benzamide;
4-Chloro-N-[4-(4,5-dihydro-1H-imidazol-2-ylamino)-benzyl]-benzamide;
N-[4-(4,5-Dihydro-1H-imidazol-2-ylamino)-benzyl]-4-thiophen-3-yl-benzamide;
N-[4-(4,5-Dihydro-1H-imidazol-2-ylamino)-benzyl]-4-(2-methoxy-ethoxy)-benzamide;
N-[4-(4,5-Dihydro-1H-imidazol-2-ylamino)-benzyl]-4-(tetrahydro-pyran-4-yloxy)benzamide;
4-{4-[4-(4,5-Dihydro-1H-imidazol-2-ylamino)-benzylcarbamoyl]-phenoxy}-piperidine-1-carboxylic acid ethyl ester;
N-[4-(4,5-Dihydro-1H-imidazol-2-ylamino)-benzyl]-4-pyrazol-1-yl-benzamide;
N-[4-(4,5-Dihydro-1H-imidazol-2-ylamino)-benzyl]-4-(3-methyl-pyrazol-1-yl)-benzamide;
N-[4-(4,5-Dihydro-1H-imidazol-2-ylamino)-benzyl]-4-methoxy-N-methyl-benzamide;
4-(4-Benzenesulfonyl-piperazin-1-yl)-N-[4-(4,5-dihydro-1H-imidazol-2-ylamino)-benzyl]-benzamide;
4-{4-[4-(4,5-Dihydro-1H-imidazol-2-ylamino)-benzylcarbamoyl]-phenyl}-piperazine-1-carboxylic acid ethyl ester;
N-[4-(4,5-Dihydro-1H-imidazol-2-ylamino)-benzyl]-4-trifluoromethyl-benzamide; and
N-[4-(4,5-Dihydro-1H-imidazol-2-ylamino)-benzyl]-4-pyrimidin-2-yl-benzamide.

61. A pharmaceutical composition comprising a therapeutically effective amount of at least one compound of claim 1 in admixture with at least one pharmaceutically acceptable carrier.

62. A method of treatment of a disease that is mediated by an IP receptor antagonist, the method comprising administering to a subject in need of such treatment a therapeutically effective amount of at least one compound of claim 1.

63. The method of claim 62, wherein the disease state is a urinary tract disease state.

64. A method for preparing a compound of claim 1, said method comprising:

reacting a compound of the formula:

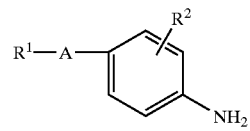

with chloroimidazoline, to form a compound of the formula:

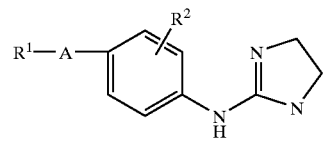

wherein $R^1$, $R^2$ and A are as defined in claim 1.

* * * * *